US012735714B2

(12) United States Patent
Koh et al.

(10) Patent No.: US 12,735,714 B2
(45) Date of Patent: Sep. 15, 2026

(54) ENGINEERED DYSBIOSIS-SENSING PROBIOTIC FOR CLOSTRIDIUM DIFFICILE INFECTIONS AND RECURRING INFECTIONS MANAGEMENT

(71) Applicant: NATIONAL UNIVERSITY OF SINGAPORE, Singapore (SG)

(72) Inventors: Elvin Koh, Singapore (SG); In Young Hwang, Singapore (SG); Matthew Wook Chang, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 1253 days.

(21) Appl. No.: 17/599,998

(22) PCT Filed: Apr. 2, 2020

(86) PCT No.: PCT/SG2020/050204
§ 371 (c)(1),
(2) Date: Sep. 29, 2021

(87) PCT Pub. No.: WO2020/204836
PCT Pub. Date: Oct. 8, 2020

(65) Prior Publication Data

US 2022/0106603 A1 Apr. 7, 2022

(30) Foreign Application Priority Data

Apr. 2, 2019 (SG) .......................... 10201902947W

(51) Int. Cl.
*C12N 15/70* (2006.01)
*A61K 35/742* (2015.01)
(Continued)

(52) U.S. Cl.
CPC ............ *C12N 15/75* (2013.01); *A61K 35/742* (2013.01); *A61K 35/747* (2013.01); *A61K 45/06* (2013.01); *A61P 31/04* (2018.01); *C12N 1/205* (2021.05); *C12N 15/111* (2013.01); *C12N 15/70* (2013.01); *C12N 15/74* (2013.01); *C12R 2001/19* (2021.05)

(58) Field of Classification Search
None
See application file for complete search history.

(56) References Cited

FOREIGN PATENT DOCUMENTS

| | | | |
|---|---|---|---|
| WO | 2015/179437 | A1 | 11/2015 |
| WO | 2017123592 | A1 | 7/2017 |

OTHER PUBLICATIONS

Strych et al., Current Microbiology , 2000, vol. 41, pp. 290-294 (Year: 2000).*

(Continued)

*Primary Examiner* — Manjunath N Rao
*Assistant Examiner* — Qing Xu
(74) *Attorney, Agent, or Firm* — Meunier Carlin & Curfman LLC

(57) ABSTRACT

The present invention relates to methods of metabolic engineering bacteria cells to produce bile salt hydrolase to inhibit the germination of *C. difficile* endospores and colonisation within the human gastrointestinal tract. The bile salt hydrolase is operably linked to a sialic acid-inducible promoter, pNanA, of which pNanA is in turn controlled by the repressor nanR. The recombinant bacteria expressing the bile salt hydrolase can be a probiotic strain to be used for prophylaxis or treatment of *C. difficile* infection.

25 Claims, 19 Drawing Sheets

Specification includes a Sequence Listing.

(51) Int. Cl.

| | |
|---|---|
| ***A61K 35/747*** | (2015.01) |
| ***A61K 45/06*** | (2006.01) |
| ***A61P 31/04*** | (2006.01) |
| ***C12N 1/205*** | (2026.01) |
| ***C12N 15/11*** | (2006.01) |
| ***C12N 15/74*** | (2006.01) |
| ***C12N 15/75*** | (2006.01) |
| *C12R 1/19* | (2006.01) |

(56) References Cited

OTHER PUBLICATIONS iGEM, Registry of Standard Biological Parts, iGem repository: Collection of parts deposited during International Genetically Engineered Machine (iGEM), 2016, URL, http://parts.igem.org/2016 (Year: 2016).*
Vimr et al. Microbiol. Mole. Bio. Rev., 2004, 68(1), pp. 132-153 (Year: 2004).*
Ley, "The sweet tooth of Clostridium difficile" Nature Medicine, vol. 20, No. 3, 248-249 (2014).
Peters, et al. "Development of N-acetylneuraminic acid responsive biosensors based on the transciptional regulator NanR" Biotechnology and Bioengineering, vol. 155, 1855-1865 (2018).
Chuan, "Probiotics Engineering for the Treatment and Prevention of Gastrointestinal Infections" 2018, 189 pages.
Chuan, "Probiotics Engineering for the Treatment and Prevention of Gastrointestinal Infections" 2018, 4 pages.
Begley et al. (2005) "The Interaction Between Bacteria and Bile", FEMS Microbiology Reviews. 29(4):625-651.
Buffie et al. (2015) "Precision Microbiome Reconstitution Restores Bile Acid Mediated Resistance to Clostridium Difficile", Nature, 517(7533):205-208.
Carter et al. (2015) "Defining the Roles of TcdA and TcdB in Localized Gastrointestinal Disease, Systemic Organ Damage, and the Host Response during Clostridium difficile Infections", mBio, 6(3):e00551(10 pages).
Chen et al. (2008) "A Mouse Model of Clostridium difficile-Associated Disease", Gastroenterology, 135(6):1984-1992.
Chilton et al. (2018) "Microbiologic Factors Affecting Clostridium Difficile Recurrence", Clinical Microbiology and Infection, 24(5):476-482.
Coleman et al. (1995) "Cloning and Characterization of a Conjugated Bile Acid Hydrolase Gene From Clostridium Perfringens", Applied and Environmental Microbiology, 61(7):2514-2520.
Gebhart et al. (2015) "A Modified R-Type Bacteriocin Specifically Targeting Clostridium difficile Prevents Colonization of Mice without Affecting Gut Microbiota Diversity", mBio, 6(2):e02368-14(13 pages).
Gupta et al. (2016) "Does Alkaline Colonic pH Predispose to Clostridium difficile Infection?", Southern Medical Journal, 109(2):91-96.
Huang et al. (2015) "Sialic Acid Catabolismrives Intestinal Inflammation and Microbial Dysbiosis in Mice", 6:8141 (11 pages).
Hwang et al. (2017) "Engineered Probiotic Escherichia Coli Can Eliminate and Prevent Pseudomonas Aeruginosa Gut Infection in Animal Models", Nature Communications, 8:15028(11 pages).
Isabella et al. (2018) "Development of a Synthetic Live Bacterial Therapeutic for the Human Metabolic Disease Phenylketonuria", Nature Biotechnology, 36(9):857-864.
Kalivoda et al. (2003) "Regulation of Sialic Acid Catabolismby the DNA Binding Protein NanR in *Escherichia coli*", Journal of Bacteriology, 185(16):4806-4815.
Keseler et al. (2013) "EcoCyc: Fusing Model Organism Databases with Systems Biology", Nucleic Acids Research, 41(Database issue):D605-612.
Ley, Ruth E. (2014) "The Sweet Tooth of Clostridium Difficile", Nature Medicine, 20(3):248-249.
Maurer et al. (2015) "Gastrointestinal pH and Transit Time Profiling in Healthy Volunteers Using the IntelliCap System Confirms lleo-Colonic Release of ColoPulse Tablets", PLoS One, 10(7):e0129076(17 pages).
May et al. (1994) "Effect of Fiber Source on Short-chain Fatty Acid Production and on the Growth and Toxin Production by Clostridium Difficile", Scandinavian Journal of Gastroenterology, 29(10):916-922.
Nelson et al. (2017) "Antibiotic Treatment for Clostridium Difficile-associated Diarrhoea in Adults", Cochrane Database of Systematic Reviews, 3(3):CD004610(56 pages).
O'Toole et al. (2017) "Next-generation Probiotics: the Spectrum From Probiotics to Live Biotherapeutics", Nat. Microbiol., 2:17057(6 pages).
Packey et al. (2009) "Commensal Bacteria, Traditional and Opportunistic Pathogens, Dysbiosis and Bacterial Killing in Inflammatory Bowel Diseases", Current Opinion in Infectious Diseases, 22(3):292-301.
Petrosillo, N. (2018) "Tackling the Recurrence of Clostridium Difficile Infection", Médecine et Maladies Infectieuses, 48(1):18-22.
Ridlon et al. (2006) "Bile Salt Biotransformations by Human Intestinal Bacteria", Journal of Lipid Research, 47 (2):241-259.
Ridlon et al. (2012) "Identification and Characterization of Two Bile Acid Coenzyme a Transferases from Clostridium Scindens , A Bile Acid 7 a-dehydroxylating Intestinal Bacterium", Journal of Lipid Research, 53(1):66-76.
Roberts et al. (2010) "Clostridium Difficile: No Longer an Enigmatic Pathogen?", Methods in Molecular Biology, 646:3-7.
Schultz et al. (2008) "Clinical Use of *E. coli* Nissle 1917 in Inflammatory Bowel Disease", Inflammatory Bowel Diseases, 14(7):1012-1018.
Shelby et al. (2020) "Development of a Standardized Scoring System to Assess a Murine Model of Clostridium difficile Colitis", Journal of Investigative Surgery, 33(10):887-895.
Sonnenborn et al. (2009) "The Non-pathogenic *Escherichia coli* Strain Nissle 1917—Features Of a Versatile Probiotic", Microbial Ecology in Health and Disease, 21:122-158.
Sorg et al. (2008) "Bile Salts and Glycine as Cogerminants for Clostridium difficile Spores", Journal of Bacteriology, 190(7):2505-2512.
Watson et al. (1992) "Identification of Elements Involved in Transcriptional Regulation the *Escherichia coli* cad Operon by External pH", Journal of Bacteriology, 174(2):530-540.
Singapore Search Report and Written Opinion issued in corresponding SG application 11202110564W, dated Feb. 1, 2022 (8 Pages).
International Search Report and Written Opinion received for PCT Application No. PCT/SG2020/050204, mailed on Sep. 10, 2020, 6 pages.
Peters, G. et al., "Development of N-acetylneuraminic acid responsive biosensors based on the transcriptional regulator NanR", Biotechnol Bioeng, Mar. 13, 2018, vol. 115, No. 7, pp. 1855-1865.
Ng K.M. et al., "Microbiota-liberated host sugars facilitate post-antibiotic expansion of enteric pathogens", Nature, Oct. 3, 2013, vol. 502, No. 7469, pp. 96-99.
Ley R. E., "Hamessing microbiota to kill a pathogen: The sweet tooth of Clostridium difficile", Nat. Med., Mar. 4, 2014, vol. 20, No. 3, 248-249.
Kuper, C. and Jung, K., CadC-mediated activation of the CadBA promoter in *Escherichia coli.* J Mol Microbiol Biotechnol, Feb. 17, 2006, vol. 10, No. 1, pp. 26-39.

* cited by examiner

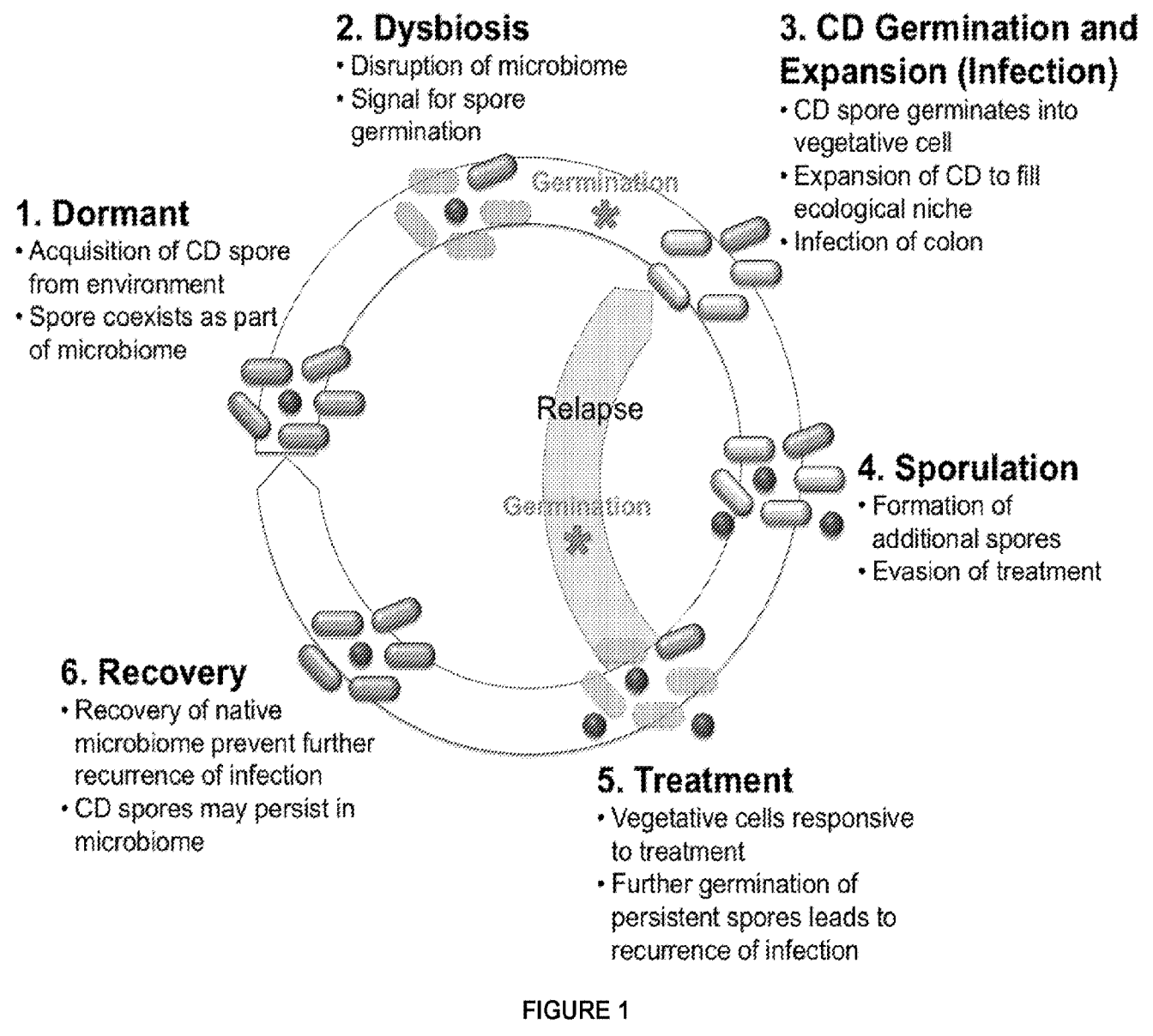

1. Dormant
• Acquisition of CD spore from environment
• Spore coexists as part of microbiome 2. Dysbiosis
• Disruption of microbiome
• Signal for spore germination 3. CD Germination and Expansion (Infection)
• CD spore germinates into vegetative cell
• Expansion of CD to fill ecological niche
• Infection of colon 4. Sporulation
• Formation of additional spores
• Evasion of treatment 5. Treatment
• Vegetative cells responsive to treatment
• Further germination of persistent spores leads to recurrence of infection 6. Recovery
• Recovery of native microbiome prevent further recurrence of infection
• CD spores may persist in microbiome Germination Relapse Germination

FIGURE 1

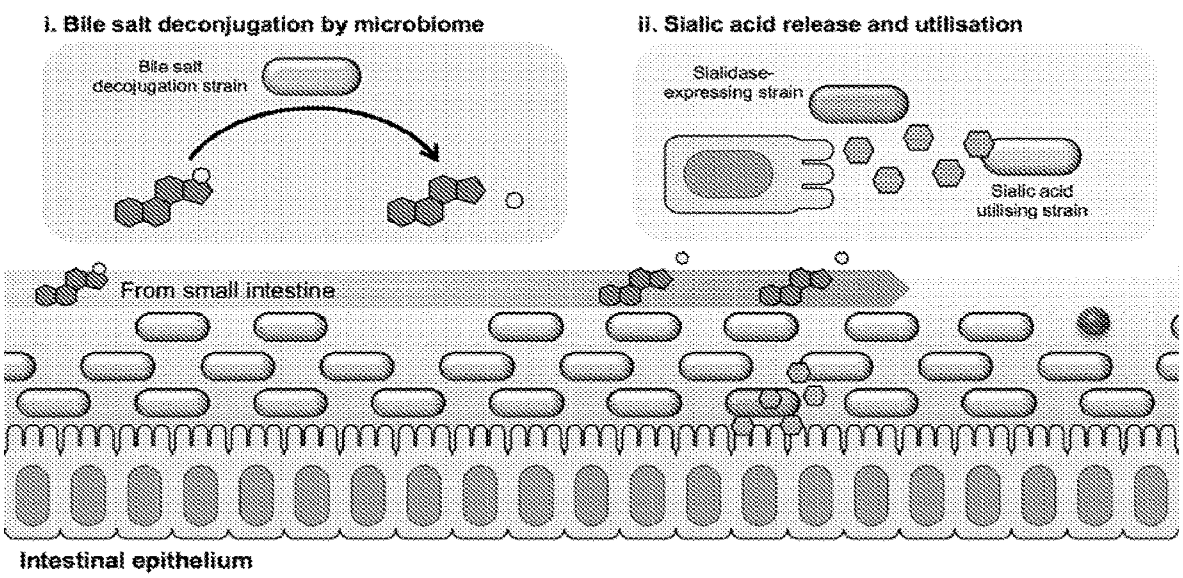
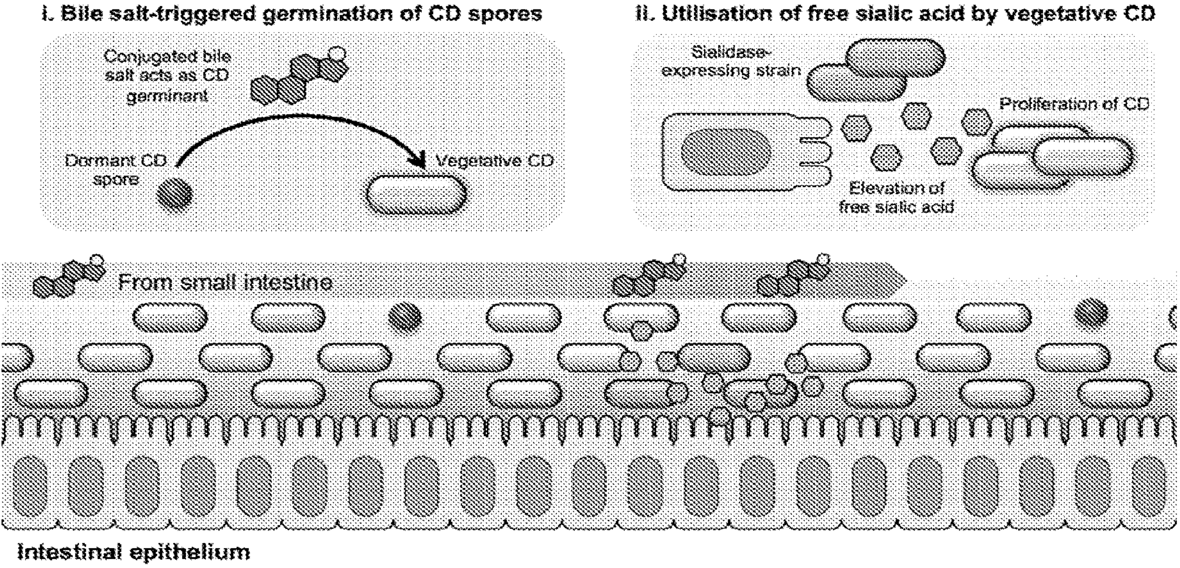
FIGURE 3

ENGINEERED DYSBIOSIS-SENSING PROBIOTIC FOR CLOSTRIDIUM DIFFICILE INFECTIONS AND RECURRING INFECTIONS MANAGEMENT

CROSS-REFERENCES TO RELATED APPLICATIONS

This application is a U.S. National Phase Application of PCT International Application No. PCT/SG2020/050204, filed Apr. 2, 2020, which is an International Application of and claims the benefit of priority to SG Patent Application No. 10201902947W, filed on Apr. 2, 2019 the entire contents of which are herein incorporated by reference.

FIELD OF THE INVENTION

The present invention relates to methods of metabolic engineering cells to produce bile salt hydrolase to inhibit the germination of *C. difficile* endospores and colonisation within the human gastrointestinal tract, a probiotic, and methods of prophylaxis or treatment of *C. difficile* infection.

BACKGROUND OF THE INVENTION

*Clostridium difficile* (also classified as *Clostridioides difficile*) are pathogens responsible for causing *C. difficile* infections (CDIs) and recurring CDIs (rCDIs). CDI is one of the common hospital-acquired infections worldwide. However, treatment of CDIs is difficult due to formation of bacterial endospores which evade antibiotic treatment. Recurrence of CDI occurs in 20.9% of the patients and mortality rate due to these infections is at 9.3%. The germination of dormant endospores that follows disruption of the native microbiome, or dysbiosis, is postulated to lead to the infections as well as the recurrences (FIG. 1). The germination of endospores is predominantly facilitated by bile salt taurocholate in the human gastrointestinal tracts. Dysbiosis of the microbiome in the human gastrointestinal tracts are postulated to lead to an increase in amount of free taurocholate and facilitate the germination of the endospores.

Fecal microbiota transplantation (FMT) is an experimental treatment for CDIs. In FMT, liquid stool suspension extracted from a healthy donor is infused to patient suffering from CDI. It aims to restore the microbiota balance in the gastrointestinal tract. While disease prognosis generally improved, adaptation of the treatment is limited. This is in part due to safety concerns with the use of fecal matters. Furthermore, this strategy is a form of black box engineering that does not identify the specific species of the microbiome necessary to inhibit the infection. The mechanism behind the improvement in prognosis is largely unknown aside from being assumed to be bulk replacement of the disrupted microbiome.

SUMMARY OF THE INVENTION

This invention takes the form of an engineered probiotic strain that can inhibit the germination of *C. difficile* endospores within the human gastrointestinal tract. The probiotic expresses bile salt hydrolase that deconjugates *C. difficile* endospore germinant taurocholate into cholate. In contrast to taurocholate, cholate has a lower endospore germination efficiency. Furthermore, cholate exhibits growth inhibition on vegetative *C. difficile*. These result in an inhibition of endospore germination as well as a retardation of the onset of *C. difficile* proliferation and colonisation (FIG. 2). Recovery of microbiome during this delay can prevent CDIs and rCDIs. The probiotic is further augmented to respond to dysbiosis of the microbiome. Dysbiosis was reported to cause elevated free sialic acid level in the gastrointestinal tract. The expression of bile salt hydrolase is placed under the control of sialic acid-responsive element. This enables timely expression of bile salt hydrolase upon changes in the microbiome. In addition, the expression of the enzyme through probiotic delivery chassis enables long-term and robust expression through colonisation within the human gastrointestinal tract. This invention was shown to inhibit the germination of *C. difficile* by 97.8% in vitro compared to untreated control.

This invention is of clinical relevance. It addresses the prophylactic needs against CDIs and rCDIs. Two groups of patients will especially benefit from this invention. Patients who are at risk of CDI, such as those who are currently on antibiotic regimes in hospital, will find it helpful as prevention against CDIs onset. It can also be administrated to current CDIs patients as prevention to rCDIs.

In a first aspect the present invention relates to an expression cassette comprising;

i) a bile salt hydrolase gene, and ii) a sialic acid-responsive promoter operably linked to the bile salt hydrolase gene.

In some embodiments the bile salt hydrolase gene is a Cbh protein-encoding polynucleotide sequence from *Clostridium perfringens*, preferably encoding the amino acid sequence set forth in SEQ ID NO: 13 or a functional variant thereof.

In some embodiments the bile salt hydrolase polynucleotide sequence comprises a nucleic acid sequence that has at least 80%, at least 85%, at least 90%, at least 95% sequence identity or 100% sequence identity to the nucleic acid sequence set forth in SEQ ID NO: 8 or SEQ ID NO: 9.

It would be understood that due to the redundancy in the genetic code, a polynucleotide sequence may have less than 100% identity and still encode the same amino acid sequence, such as the amino acid sequence of bile salt hydrolase set forth in SEQ ID NO: 13.

In some embodiments the sialic acid-responsive promoter is pNanA from *E. coli*, preferably comprising the nucleic acid sequence set forth in SEQ ID NO: 4 or a functional variant thereof.

In some embodiments a repressor of pNanA is positioned upstream of pNanA when there is expression of pNanA in the absence of sialic acid, wherein preferably the repressor is a NanR protein-encoding polynucleotide sequence, preferably encoding the amino acid sequence set forth in SEQ ID NO: 11 or a functional variant thereof.

In some embodiments the NanR protein-encoding polynucleotide sequence comprises a nucleic acid sequence that has at least 80%, at least 85%, at least 90%, at least 95% sequence identity or 100% sequence identity to the nucleic acid sequence set forth in SEQ ID NO: 5.

In some embodiments, the cassette further comprises a constitutive promoter operably linked to NanR, wherein the promoter is selected from the group comprising pBad with AraC; J23108 with rbs2, rbs3 or rbs5; and J23113 with rbs4.

In some embodiments the constitutive promoter operably linked to NanR is J23113-rbs4.

In some embodiments the cassette comprises J23113-rbs4-NanR, preferably comprising the nucleic acid sequence set forth in SEQ ID NO: 6 or a functional variant thereof.

In some embodiments, the cassette further comprises an activator and promoter to increase the expression of Cbh, such as the transcription activator CadC protein-encoding sequence and promoter pCadBA, wherein CadC is positioned downstream and under the control of pNanA and pCadBA is positioned downstream of CadC and operably linked to the bile salt hydrolase Cbh protein-encoding sequence.

In some embodiments, the CadC amino acid sequence is set forth in SEQ ID NO: 12 or a functional variant thereof. In some embodiments, the CadC nucleic acid sequence is set forth in SEQ ID NO: 14 or a functional variant thereof.

In some embodiments, the activator and promoter nucleic acid sequence comprises the nucleic acid sequence set forth in SEQ ID NO: 7 or a functional variant thereof.

In some embodiments, the cassette is comprised in one or more plasmid vectors.

In some embodiments, the plasmid vector is pEaat, preferably comprising the nucleic acid sequence set forth in SEQ ID NO: 1. This vector comprises an origin of replication, alr selection marker (SEQ ID NO: 2 and 3), kanamycin resistance marker, and multiple cloning sites.

In some embodiments, the cassette further comprises an antibiotic resistance gene flanked by FRT sites to enable its removal.

In some embodiments, the gene polynucleotide sequence for cbh is codon-optimised for expression in a probiotic cell. An example of a codon-optimised gene sequence for cbh is the nucleic acid sequence set forth in SEQ ID NO: 9.

In some embodiments, the gene polynucleotide sequence for cbh is codon-optimised for expression in a probiotic cell selected from the group comprising *E. coli* sp., *Bacteroides* sp., *Clostridium* sp., *Faecalibacterium* sp., *Lactococcus lactis*, and *Lactobacillus* sp.

In another aspect of the invention there is provided a use of an expression cassette according to any aspect of the invention for the recombinant production of bile salt hydrolase proteins.

In another aspect of the invention there is provided a composition comprising:

a) a probiotic bacteria; and
b) an expression cassette according to any aspect of the invention, wherein the probiotic bacteria comprises the expression cassette for production of bile salt hydrolase.

The probiotic bacteria may be selected from any suitable genera of probiotic bacteria.

In some embodiments, the probiotic bacteria is selected from the group comprising *E. coli* sp., *Bacteroides* sp., *Clostridium* sp., *Faecalibacterium* sp., *Lactococcus lactis*, and *Lactobacillus* sp.

In some embodiments, the probiotic bacteria is auxotrophic.

In some embodiments, the auxotrophic bacteria has had Alanine racemase genes deleted and cannot divide in the absence of D-Alanine.

In another aspect of the invention there is provided a composition according to any aspect of the invention for use in a method of treating *C. difficile* infections (CDIs) and/or recurring CDIs (rCDIs).

In some embodiments, the CDIs and/or rCDIs are caused by dysbiosis.

In another aspect of the invention there is provided a method of treatment or prophylaxis comprising administering to a subject in need of such treatment or prophylaxis an efficacious amount of a composition according to any aspect of the invention.

In some embodiments, the subject has a *C. difficile* infection (CDI) or recurring CDI.

In another aspect of the invention there is provided a composition according to any aspect of the invention for the manufacture of a medicament for the treatment or prophylaxis of CDI and/or rCDI.

In some embodiments, the *C. difficile* infection (CDI) and/or recurring CDI is due to dysbiosis.

BRIEF DESCRIPTION OF THE FIGURES

FIG. 1 shows a schematic of dysbiosis-induced infections and recurrent infections of *C. difficile*. 1) *C. difficile* (CD) endospores acquired from the environment can exist as dormant member of microbiome. 2) Disruption of normal microbiome produces ecological niches for *C. difficile* colonisation. 3) Endospores germinate into vegetative cells and further expand into ecological niches within the microbiome leading to infection of the host. 4) At later stage of infection, additional endospores will be produce by the vegetative cells. 5) These endospores are able to evade antibiotics treatment. The continued dysbiosis of microbiome provides window of vulnerability for recurrent infection as endospores can germinate once treatment ceases. 6) Even with recovery from infection, endospores may still persist and trigger the infection when dysbiosis occurs.

FIG. 3 shows a proposed model for the mechanisms of dysbiosis-induced *C. difficile* infections. Two groups of microorganisms in the microbiome (top) are disrupted in event of dysbiosis (bottom). i) The first group mediates the deconjugation of bile salts from small intestine (SI). The loss of this group of microorganism during dysbiosis results in conjugated bile salts in colon where *C. difficile* (CD) endospores reside. Conjugated bile salts trigger the germination of endospores into vegetative *C. difficile*. ii) The second group comprising of sialic acid utilising species and sialidase-expressing species regulate free sialic acid level within the gastrointestinal tract. The upset in balance of the species during dysbiosis results in elevation of sialic acids. Germinated *C. difficile* are able to utilise the sialic acids as carbon source for their expansion leading to infection of the host.

DEFINITIONS

Figure 2:
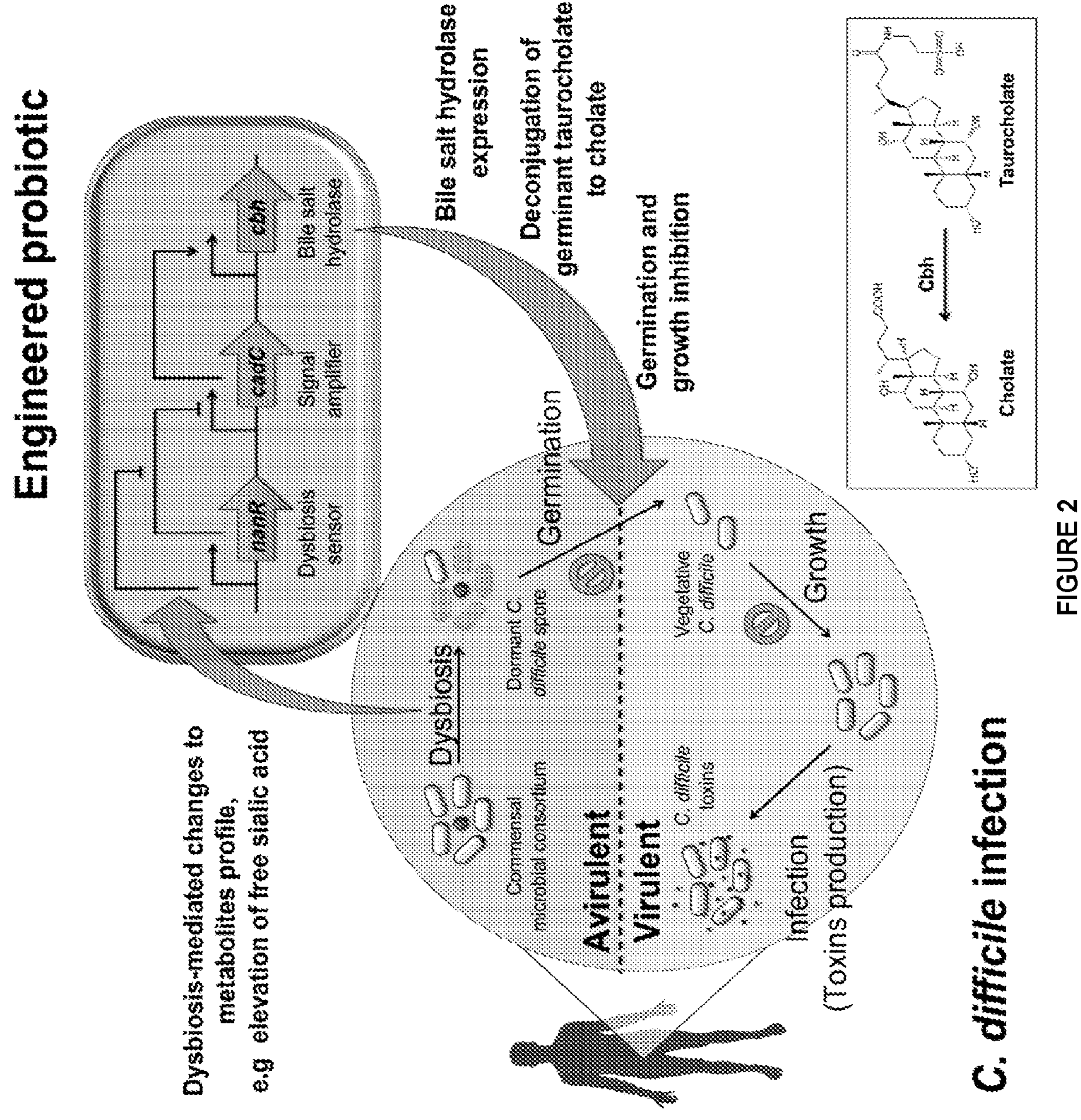
FIG. 2 shows a schematic of a strategy employed by the invention to achieve inhibition of *C. difficile* endospores. Dysbiosis of the microbiome changes metabolite profile in the gastrointestinal tract. This includes elevated level of free sialic acids. Engineered probiotics are activated by sialic acids to express bile salt hydrolases. The enzymes are able to deconjugate *C. difficile* endospore germinant taurocholate into a weaker germinant cholate. Inhibition of *C. difficile* endospores germination is hence achieved, and transition from avirulent to virulent form of *C. difficile* prevented.

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "functional variant" or "variant" as used herein, refers to an amino acid sequence that is altered by one or more amino acids, but retains the same function as the non-variant reference sequence, for example bile salt hydrolase. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR® software (DNASTAR, Inc. Madison, Wis., USA).

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

The term "probiotic", as used herein, refers to a viable microbial supplement, which has a beneficial influence on a patient through its effects in the intestinal tract, urinary tract or the vaginal tract.

The term "prophylaxis", as used herein refers to treatment given or action taken to prevent disease, such as prevention of CDI-linked disease.

The term "treatment", as used in the context of the invention refers to ameliorating, therapeutic or curative treatment.

The term "subject" is herein defined as vertebrate, particularly mammal, more particularly human. For purposes of research, the subject may particularly be at least one animal model, e.g., a mouse, rat and the like. In particular, for treatment or prophylaxis of dysbiosis, more particularly CDI-linked diseases, the subject may be a human.

DETAILED DESCRIPTION OF THE INVENTION

Bibliographic references mentioned in the present specification are for convenience listed at the end of the examples. The whole content of such bibliographic references is herein incorporated by reference.

The general consensus on the mechanisms of CDI and rCDI involves the dysbiosis of microbiome and subsequent germination of dormant endospores as a result (FIG. 1) [Petrosillo, N. *Med. Mal. Infect.* 48(1): 18-22 (2018)]. In normal healthy microbiome, *C. difficile* may remain as commensal dormant endospores in the human gastrointestinal tracts without causing infection due to lack of ecological niche. Paradoxically, administration of broad-spectrum antibiotics has been established to be a risk factor that promotes CDI [Petrosillo, N. *Med. Mal. Infect.* 48(1): 18-22 (2018); Roberts, A. P., & Mullany, P. *Clostridium difficile*: methods and protocols. Ed: P. Mullany, A. Roberts. Springer US, New York. 3-8 (2010)]. Administration of antibiotics is postulated to upset the balance of existing microbiome and lead to dysbiosis [Gebhart, D., et al. *mBio.* 6(2): doi: 10.1128/mBio.02368-14 (2015)]. *C. difficile*, either from the germinated dormant endospores or newly acquired from the environment, can exploit this opportunity to rapidly expand to virulence load leading to infection [Gebhart, D., et al. *mBio.* 6(2): doi: 10.1128/mBio.02368-14 (2015); Sorg, J. A., & Soenenshein, A. L. *J. Bacteriol.* 190(7): 2505-12 (2008)]. Compounding the problem, in addition to antimicrobial resistance that arises due to selection pressure from antibiotic treatments, *C. difficile* endospores are naturally resistant to antibiotics [Petrosillo, N. *Med. Mal. Infect.* 48(1): 18-22 (2018); Roberts, A. P., & Mullany, P. *Clostridium difficile*: methods and protocols. Ed: P. Mullany, A. Roberts. Springer US, New York. 3-8 (2010)]. This enables the endospores to evade eradication treatment, and is suspected to be a cause of rCDI through relapse following the window of vulnerability until the microbiome homeostasis recovers [Petrosillo, N. *Med. Mal. Infect.* 48(1): 18-22 (2018)].

Evidence suggests that bile salt metabolising species, such as *C. scindens*, within the microbiome confer colonisation resistance against *C. difficile* [Chilton, C. H., Pickering, D. S., & Freeman, *J. Clin. Microbiol. Infect*. Published ahead of print. doi: 10.1016/j.cmi.2017.11.017 (2018); Buffie, C. G., et al. *Nat. Lett.* 517: 205-8 (2015)]. Bile salts are known germinant of *C. difficile* [Sorg, J. A., & Soenenshein, A. L. *J. Bacteriol.* 190(7): 2505-12 (2008)] and disruption of bile salt metabolism due to disrupted intestinal microbiome, could result in germination leading to CDI.

In humans, bile salts are synthesised in liver and secreted into the gastrointestinal tract at the duodenum of small intestine through the gall bladder [Sorg, J. A., & Soenenshein, A. L. *J. Bacteriol.* 190(7): 2505-12 (2008)]. Bile salts exist in different molecular forms depending on their conjugates and functional groups. Discharged bile salts from the human liver exist as primary bile salt conjugated to taurine or glycine, forming taurocholate or glycocholate respectively. Taurocholate is a known germinant of *C. difficile* and is routinely utilised to induce endospores germination in laboratory manipulation of the bacteria [Sorg, J. A., & Soenenshein, A. L. *J. Bacteriol.* 190(7): 2505-12 (2008)]. It is understood that bile salts undergo modification by the microbiome as they proceed down toward lower gastrointestinal tract [Ridlon, J. M., Kang, D., & Hylemon, P. B. *J. Lipid. Res.* 47: 241-59 (2006); Begley, M., Gahan, C. G. M., & Hill, C. *FEMS. Microbiol. Rev.* 25: 625-51 (2005)]. Notably, the deconjugation of conjugated bile salts into primary unconjugated bile salts, and the 7α-dehydroxylation of primary bile salts into secondary bile salts. The latter reaction can be mediated by the previously mentioned *C. scindens* [Ridlon, J. M., & Hylemon, P. B. *J. Lipid. Res.* 53: 66-76 (2012)]. Furthermore, secondary bile salt, deoxycholate, was shown to inhibit *C. difficile* colonization [Sorg, J. A., & Soenenshein, A. L. *J. Bacteriol.* 190(7): 2505-12 (2008)]. As a result of these modifications, bile salts in colon exist predominantly as unconjugated primary or secondary forms [Sorg, J. A., & Soenenshein, A. L. *J. Bacteriol.* 190(7): 2505-12 (2008)].

A model of the mechanisms leading to CDI onset due to dysbiosis is proposed here (FIG. 3). Two events due to dysbiosis are suggested to induce CDI. It is hypothesised that dysbiosis disrupted these species in the microbiome that are involved in bile salt modification. This resulted in a dysregulation of bile salt composition in the lower gastrointestinal tract. The increased concentration of conjugated bile salt, particularly taurocholate, acts as a trigger for germination and to signify vacant ecological niches within the microbiome for *C. difficile* colonisation. The second event involves the elevation of free sialic acids in the gastrointestinal tract. Dysbiosis disruption of the microbiota leading to loss of sialic acid utilising strains and/or proliferation of sialidase-expressing strains [Ng, K. M., et al. *Nat. Lett.* 502: 96-9910 (2013)]. This causes an elevation of free sialic acids within the gastrointestinal tract. Germinated vegetative *C. difficile* utilise the free sialic acid as carbon source for further proliferation and expansion leading to CDI.

Here, we sought to invent a prophylactic antimicrobial strategy for the prevention of CDI. Through the understanding of the pathogenesis of *C. difficile*, germination of *C. difficile* endospores was identified as a potential intervention point to prevent progression of the infection. The mechanisms for the onset of infections can be exploited by engineered probiotics to modulate the germination of endospores.

Figure 4:
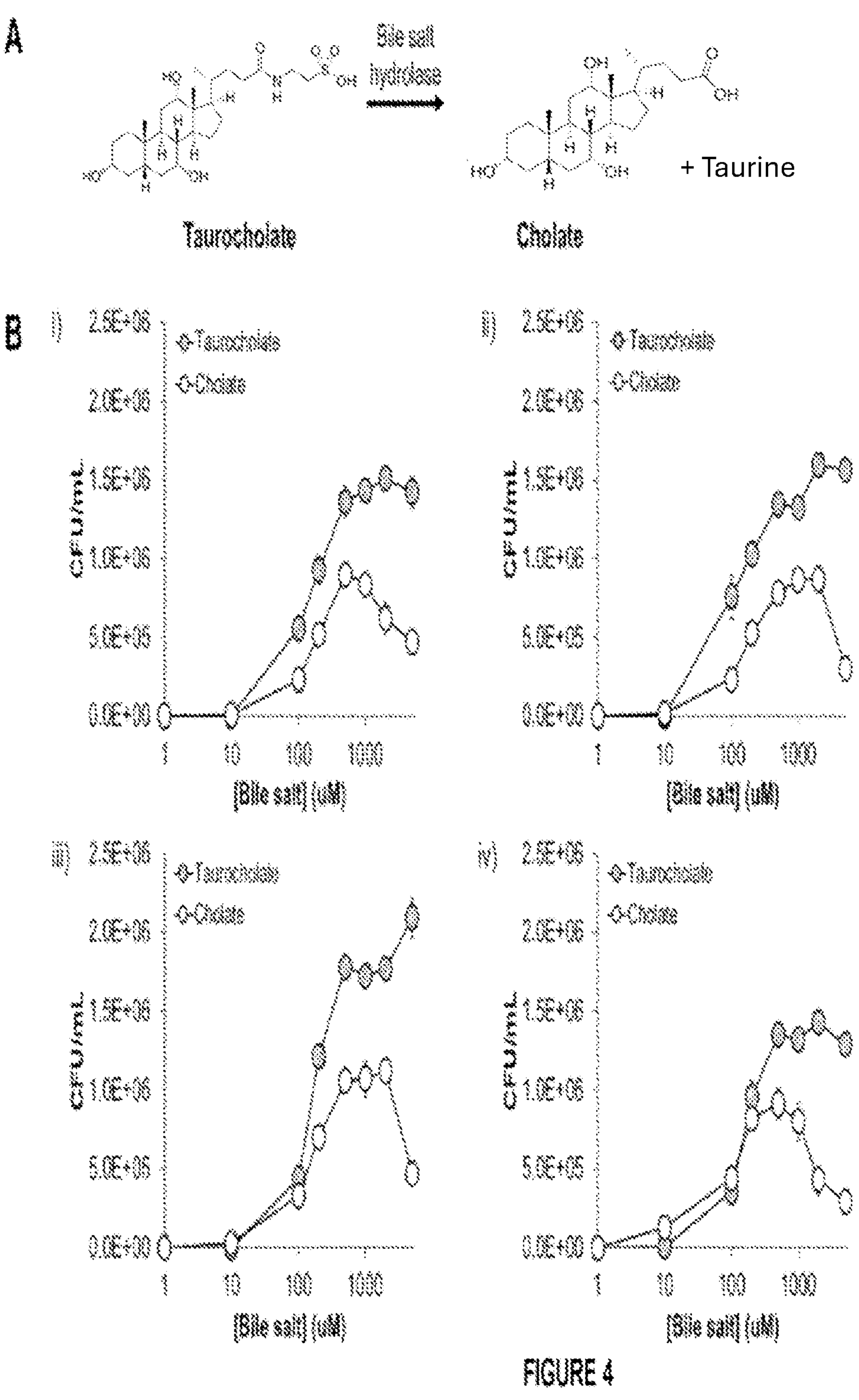
FIG. 4 shows that conjugated bile salt taurocholate is a more efficiency germinant of *C. difficile* endospores and deconjugated bile salt cholate inhibits the growth of *C. difficile*. A) Conjugated bile salt taurocholate is deconjugated by bile salt hydrolase into primary bile salt cholate and taurine. B) Germination from endospores extracted from *C. difficile* strains i) CD630, ii) VP110463, iii) BAA-1870, and iv) 9689 by incubation with taurocholate (filled circle) and cholate (blank circle) at different concentration. Error bars represent S.E.M of duplicates. C) Growth of *C. difficile* strains i) CD630, ii) VP110463, iii) BAA-1870, and iv) 9689 with taurocholate (filled circle) and cholate (blank circle).
Figure 4:
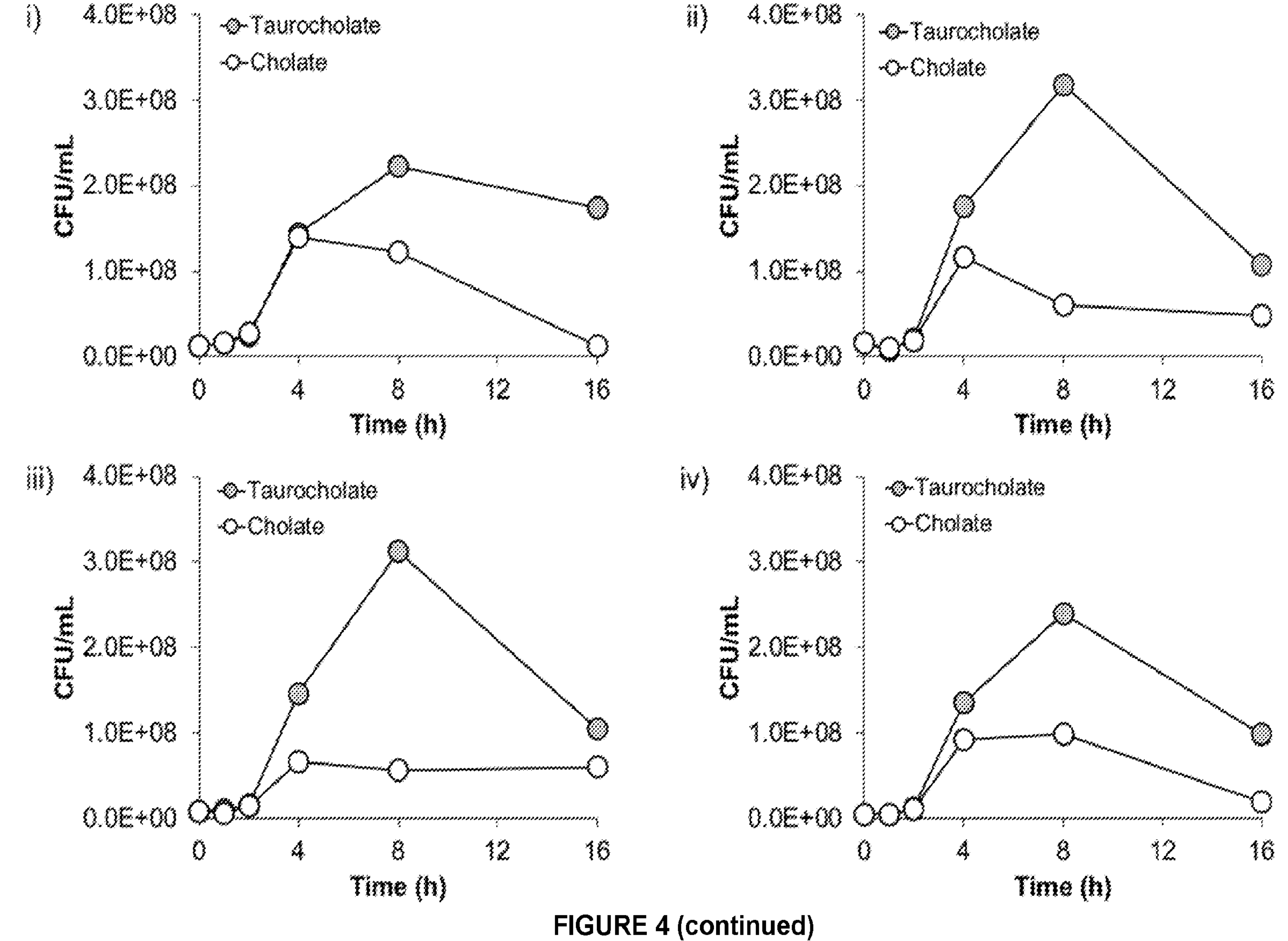

In the proposed model of mechanisms in dysbiosis-induced CDI, conjugated bile salts are hypothesised to be the driving germinant for *C. difficile* endospores germination. During homeostasis state of the microbiome, conjugated bile salts are metabolised by microbiota before reaching the colon where *C. difficile* colonise during CDI. This is disrupted during dysbiosis. As a proof-of-principle to the model, the germination efficiencies of conjugated and deconjugated bile salts were assayed. Taurocholate is deconjugated into cholate and taurine by the enzyme bile salt hydrolase (Enzyme Commission number: EC3.5.1.24) [Coleman, J. P., & Hudson, L. L. *Appl. Environ. Microbiol.* 61(7): 2514-20 (1995)] (FIG. 4A). The deconjugated bile salt displayed significantly reduced germination efficiency compared to taurocholate (FIG. 4B). Higher concentration of cholate further inhibits the germination in consistent with existing report [Sorg, J. A., & Soenenshein, A. L. *J. Bacteriol.* 190(7): 2505-12 (2008); Begley, M., et al., *FEMS. Microbiol. Rev.* 25: 625-51 (2005)]. Furthermore, cholate was shown to inhibit the growth of vegetative *C. difficile* cells (FIG. 4C). These results suggest that modulation of bile salt deconjugation to prevent the germination of *C. difficile* endospores and inhibit their subsequent growth can function as a viable prophylactic antimicrobial strategy against *C. difficile*.

We envision a prophylactic antimicrobial strategy that utilises engineered probiotic strain EcN (D-alanine auxotrophic *Escherichia coli* Nissle) [Hwang, I, Y., et al., *Nat. Commun.* 8: 15028. doi: 10.1038/ncomms15028 (2017)] to modulate the bile salt deconjugation through in vivo expression of bile salt hydrolase. This expression of bile salt hydrolase can reduce local taurocholate concentration, which in turn inhibits the germination of *C. difficile* endospores. The delay of *C. difficile* germination from endospores and growth inhibition can prevent excessive expansion leading to CDIs or rCDIs. Bile salt hydrolase, Cbh, from *Clostridium perfringens* was selected for application [Coleman, J. P., & Hudson, L. L. Appl. *Environ. Microbiol.* 61(7): 2514-20 (1995)]. The expression of the enzyme is coupled to sialic acid-responsive promoter, pNanA (SEQ ID NO: 4). Sialic acid was shown to upregulate during dysbiosis of microbiome (10). By coupling pNanA to Cbh expression, pNanA can regulate the expression of Cbh in the event dysbiosis in vivo. Under this design, when free sialic acid level is elevated during dysbiosis, pNanA will respond and express Cbh. This enables autonomous in vivo response to the onset of dysbiosis.

EcN are utilised as chassis for the delivery of the designed strategy. As gram-negative bacteria, EcN are less susceptible to gram-positive-targeting vancomycin that is commonly administrated for CDI treatment [Nelson, R. Cochrane. Database. Syst. Rev. 18(3): CD004610 (2007)]. This will permit the concurrent administration of antibiotic for treatment and probiotic for preventing rCDIs. Furthermore, EcN are able to utilise sialic acid for metabolism. As probiotic strain, they colonise as part of the microbiome. Hence, they are able to compete against the *C. difficile* for nutrient as well as vacant ecological niches within the gastrointestinal tract. In addition, the auxotrophic characteristic of EcN will enable design of plasmid that can be maintained without antibiotics. The strain has been engineered to display auxotrophic phenotype for D-alanine through the deletion of alanine racemase genes from the genome [Hwang, I, Y., et al., *Nat. Commun.* 8: 15028. doi: 10.1038/ncomms15028 (2017)]. The essential alanine racemase gene is used as a selection marker in plasmid carrying the engineered circuit. The resulting engineered strain can stably maintain designed plasmid for extended period without additional selection pressure. Taken together, the engineered EcN will confer long-term prophylactic effect against CDI in the gastrointestinal tract.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Engineering of Antibiotic Selection-Free Probiotic Chassis

One of the challenges in implementing engineered probiotics in vivo is to ensure long-term stability of genetic circuits in the chassis. Engineered genetic circuits are commonly engineered on plasmids and maintained by antibiotics selection, but such techniques are not feasible for in vivo applications. Maintenance of plasmid stability by continuous antibiotics selection cannot be conveniently implemented for colonised probiotics in the gastrointestinal tract.

Figure 5:
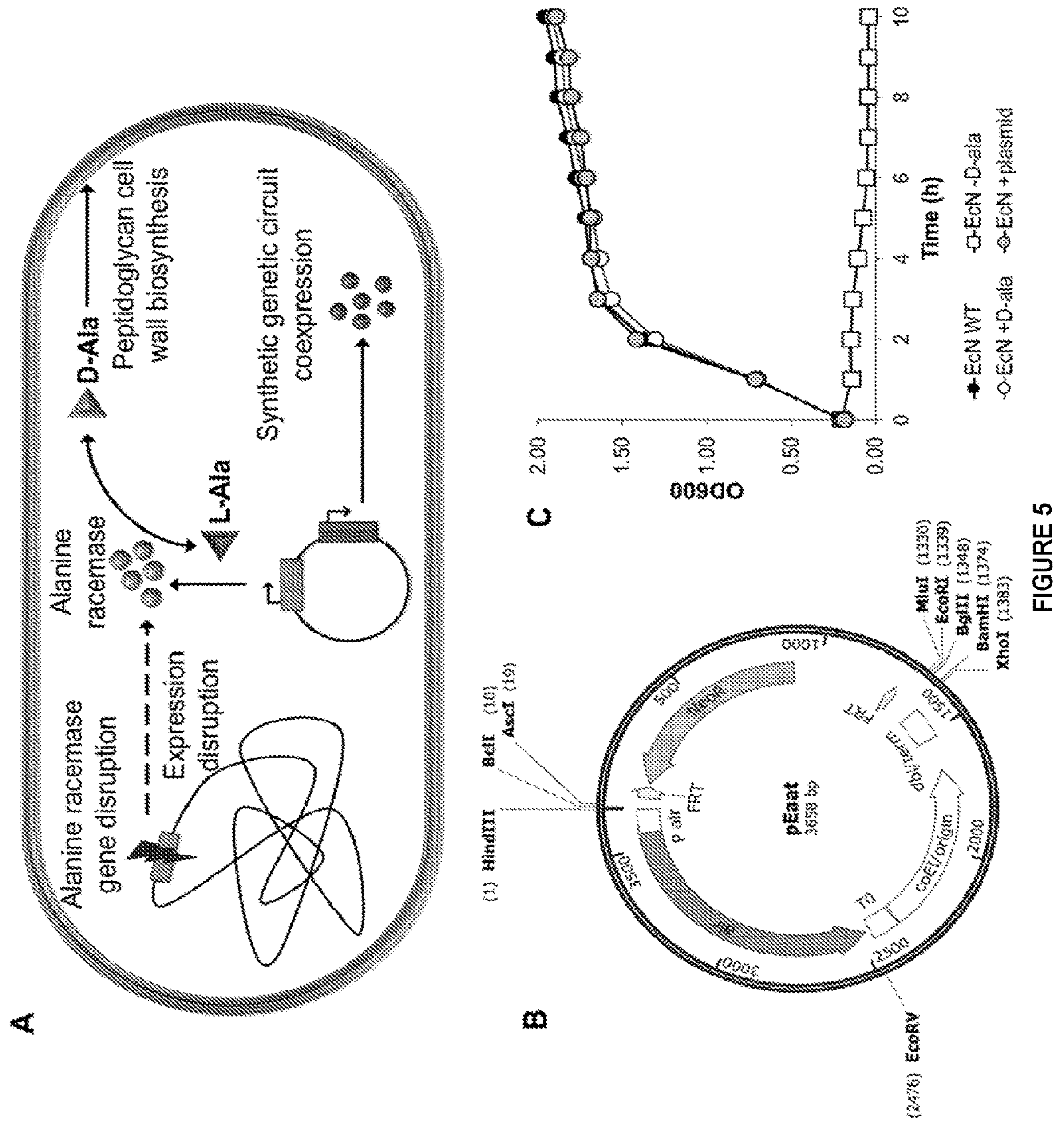
FIG. 5 shows a plan for engineering of an antibiotic selection-free probiotic chassis. A) Schematic diagram of D-alanine auxotrophic antibiotic selection-free chassis. Disruption to alanine racemase gene results in inability to produce D-alanine endogenously. Deficiency of D-alanine inhibits cell wall synthesis and cell proliferation. This phenotype can be rescued by expression of alanine racemase from plasmid. This enables selection for the plasmid and, with it, the synthetic genetic circuit. B) Plasmid map for pEaat vector (SEQ ID NO: 1). alr (SEQ ID NO: 3) encodes for alanine racemase (SEQ ID NO: 10) under control of native promoter (SEQ ID NO: 2); NeoR encodes for antibiotic resistance gene neomycin phosophotransferase. It is flanked by a pair of FRT sequences for excision via Flp; on encoded for origin of replication ColE1; nine unique restriction sites were added by design. The primary insertion site is between BglII and BamHI in accord to the BglBrick standard. C) Growth assay of ECN without (blank square) or with (blank circle) the D-alanine supplement, and phenotype rescue with pEaat plasmid (grey circle). Wild type EcN (black circle) included as control. D) Percentage of viable cells expressing neoR plasmids co-expressed on the plasmids of EcN WT expressing pBbE8K-J23108-lasR-pLas-gfp (square) or EcN expressing pEaat-J23108-lasR-pLas-gfp (triangle), with (filled) and without (blank) D-alanine supplement. Cells were subcultured daily without antibiotic selection. Viability of cell indicates presence of plasmids.
Figure 5:
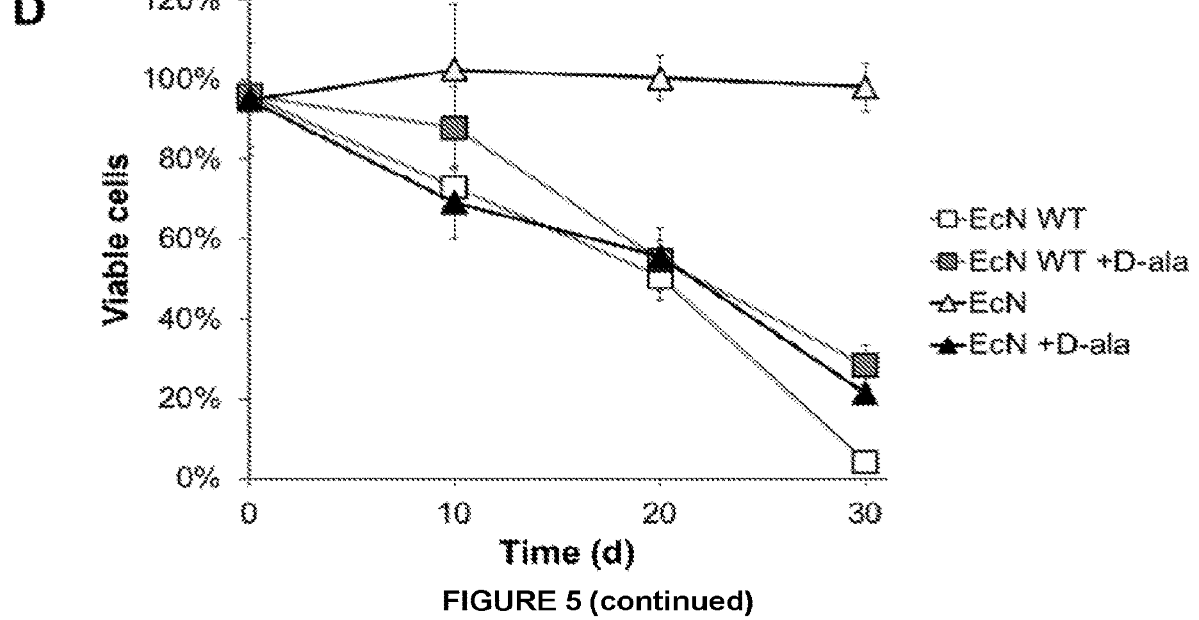

In order to enable a plasmid-chassis system that does not require antibiotic maintenance, an auxotrophic phenotype was generated in the *E. coli* Nissle wild type strain. Alanine racemase genes, which are essential for D-alanine biosynthesis were deleted from the *E. coli* Nissle genome to generate the strain EcN (FIG. 5A). D-alanine is required for the biosynthesis of bacterial cell wall. The absence of D-alanine will prevent the bacteria from further cell division, thereby creating an auxotrophic phenotype.

A plasmid was designed to rescue the auxotrophic phenotype in the EcN chassis (FIG. 5B). This plasmid contained a copy of alanine racemase to function as selection gene. It also contained a kanamycin resistance gene for characterisation and amplification purpose. This kanamycin resistance gene was flanked by FRT sites which enable the gene to be removed through the expression of Flp recombinase. This design enables the easy removal of the antibiotic resistance gene to generate a final probiotic strain that contains a self-selecting plasmid. This works to prevent potential horizontal gene transfer of resistance gene from the engineered strain into the microbiome during applications.

The alanine-deleted EcN strain successfully displayed alanine auxotrophic phenotype (FIG. 5C). The phenotype was rescued by the expression of designed plasmid pEaat. The strain was also rescued by exogenous supplementation of D-alanine. This enables the strain to be maintained in lab conditions. Furthermore, the plasmid was stably maintained in EcN for a month without the presence of any antibiotic selection (FIG. 5D). Plasmids with the antibiotic resistance gene were transformed into EcN or the wild type strain. The cells were grown in the absence of antibiotic. Cells were then tested at regular interval for the presence of plasmids. It was found that only in the engineered EcN were the plasmids maintained consistently at close to 100%. Together, these results show the applicability of EcN to function as chassis for long-term delivery of engineered genetic circuit in vivo.

Example 2

Optimisation of NanR-Dependent Sialic Acid-Inducible Promoter

Figure 6:
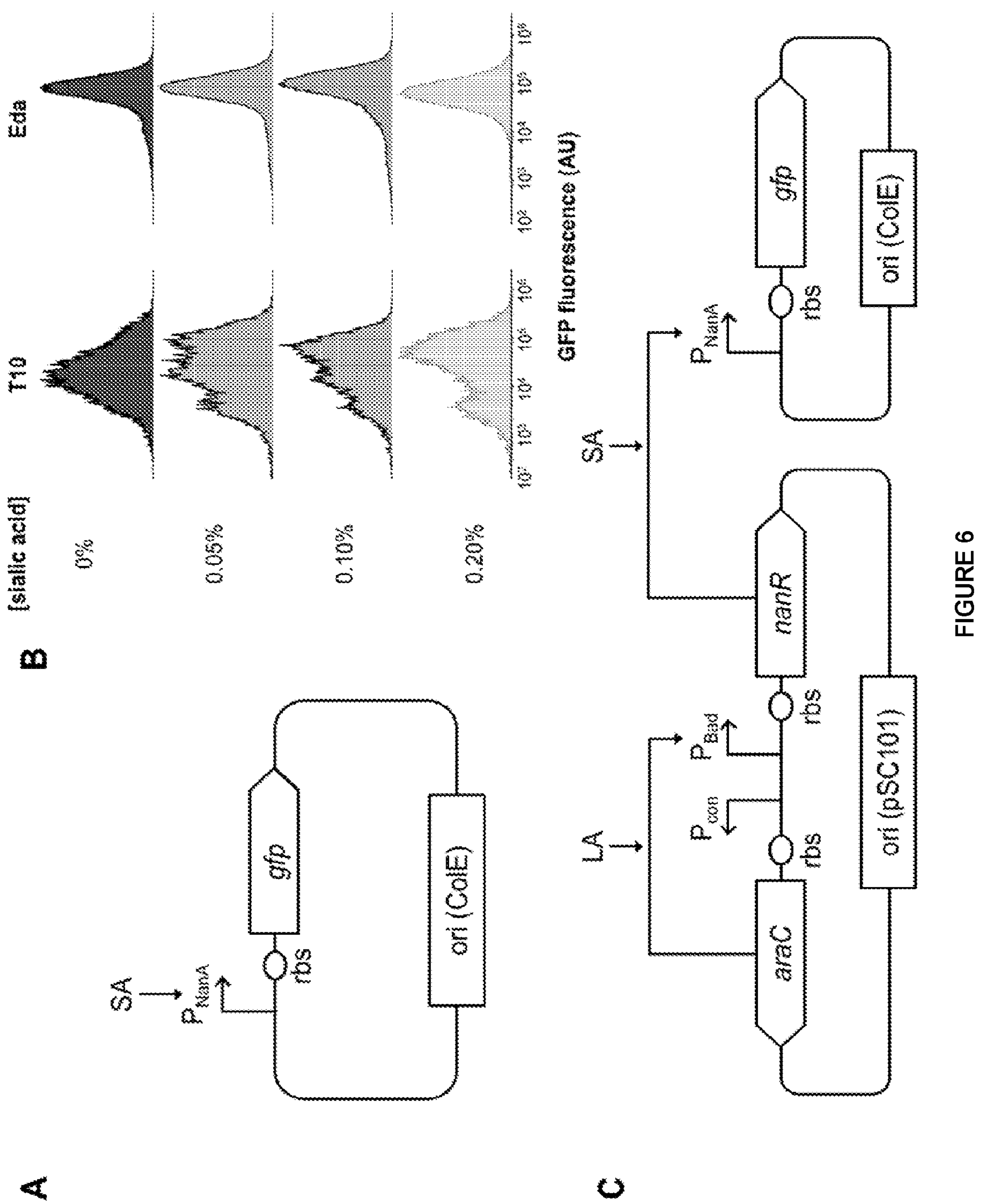
FIG. 6 shows optimisation of a NanR-dependent sialic acid inducible promoter. A) Plasmid design (pEaat-pNanA-gfp) for initial characterisation of pNanA. SA represents sialic acid induction. B) Histogram of flow cytometry fluorescence reading of 10,000 samples for pEaat-pNanA-gfp characterisation in T10 (left) and EcN (right) at various concentration of sialic acid induction. C) Plasmid design of co-expressed plasmid for characterisation of NanR (SEQ ID NO: 11) and pNanA (pSC101-pBad-nanR). LA represents L-arabinose induction; SA represents sialic acid induction. D) Matrix data of median GFP fluorescence reading of 10,000 samples on flow cytometry for each combination of sialic acid (SA) and L-arabinose (LA) induction. Colour of each cell is graded to scale. E) Plasmid design for co-expression of nanR in pEaat-pNanA-gfp. F) Optimisation of pNanA expression by modulating nanR expression. Relative GFP fluorescence expression of constructs expressing nanR under different promoter and ribosome binding site. Cells were induced with 0.2% sialic acid.
Figure 6:
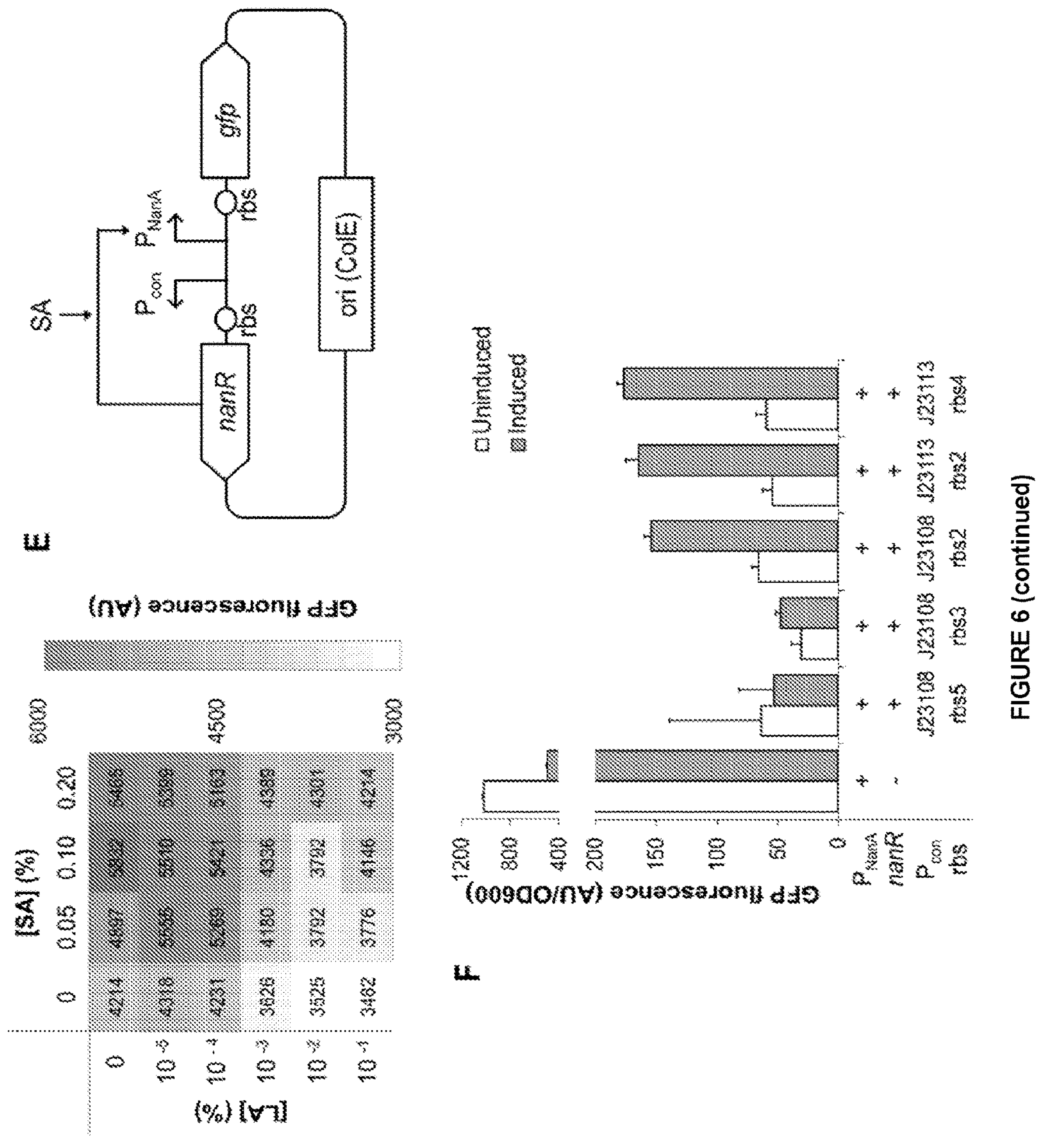

Sequence of sialic acid-inducible promoter pNanA (SEQ ID NO: 4) from MG1655 *E. coli* genome was obtained from EcoCyc database [Keseler, I. M. et al. *Nuc. Acids. Res.* 41: 605-12 (2013)]. The promoter was subcloned upstream to gfp gene in pEaat plasmid (pEaat-pNanA-gfp) and then transformed into T10 and EcN for expression characterisation (FIG. 6A). Surprisingly, the two strains of *E. coli* displayed different responses to sialic acid induction (FIG. 6B). Induction of sialic acid resulted in forward activation of T10 pNanA promoter leading to GFP expression. On the other hand, gfp under pNanA promoter in EcN was strongly expressed in the absence of sialic acid and was instead repressed with high concentration of sialic acid induction.

The difference in response suggests pNanA is regulated differently between T10 and EcN. NanR (SEQ ID NO: 5) was previously identified as a transcriptional regulator of sialic acid catabolism in *E. coli* [Kalivoda, K. A., et al., *J. Bacteriol.* 185(16): 4806-15]. The sequence of nanR in MG1655 genome (GenBank accession CP012868.1) was identified. The gene sequence along with flanking sequence 500 bp upstream and 500 bp downstream of the gene was isolated (nanR±500). BLASTn search with the nanR±500 as the query and T10 (identified as DH10P; GenBank accession CP000948.1) or Nissle (GenBank accession CP007799.1) genome sequence as the subject was performed. T10 genome sequence yielded a 100% match with the MG1655 genome. Nissle genome sequence returned a strong match of 96% against nanR sequence and 500 bp downstream. However, there is no similarity for 500 bp upstream of nanR. Regulatory element of nanR was found within 200 bp upstream of the gene. This suggests that although Nissle carries nanR sequence, its genetic regulation is disrupted in Nissle in contrast to *E. coli* of K-12 descent.

NanR was hypothesised to function as a transcriptional repressor in nan operon expression and the disrupted genomic expression of nanR in Nissle resulted in the activity of pNanA promoter observed. To test the hypothesis, nanR was subcloned from MG1655 genome into pSC101 vector under pBad promoter (pSC101-pBad-nanR) (FIG. 6C). The plasmid was co-transformed with pEaat-pNanA-gfp into EcN. The promoter pBad is regulated by a co-expressed AraC and can be induced by L-arabinose. The co-induction of L-arabinose and sialic acid in different combinations can determine the expression level of nanR required to elicit an ideal response from pNanA. The induced cells were quantified by flow cytometry for the median GFP fluorescence reading of 10,000 size-gated samples. From the results, even in the absence of L-arabinose induction, basal expression of NanR represses pNanA basal activity significantly (FIG. 6D). It also enabled pNanA promoter to be induced for expression by sialic acid. Enhanced expression of NanR reduced both pNanA basal and induced activity. This suggests that NanR is a regulator upstream of pNanA expression and only a low level of NanR is required for the regulation.

Since NanR expression is required to achieve a sialic acid-inducible response of pNanA in EcN, the genetic construct pEaat-pNanA-gfp was redesigned to co-express nanR under constitutive expression (FIG. 6E). The gene nanR was subcloned under constitutive promoter J23108 with ribosome binding site rbs5, rbs3, or rbs2. The three ribosome binding sites have different translation initiation rate, with rbs5 being the strongest and rbs2 being the weakest. The plasmids were transformed into EcN for characterisation of GFP expression with sialic acid induction. Consistent with the flow cytometry results, it was found that weak constitutive expression of NanR under ribosome binding site rbs2 showed better inductility with sialic acid (FIG. 6F). The expression of NanR was further reduced in constructs whereby the constitutive promoter was replaced with J23113 and the ribosome binding site with rbs4 (J23113-rbs4-NanR; SEQ ID NO: 6). Characterisation of GFP expression upon sialic acid induction in these constructs maintained similar expression levels compared to previous constructs despite the weaker expression of NanR.

Through the co-expression of NanR transcriptional regulator, the activity of promoter pNanA was successfully reversed from that of a repressible promoter to that of an inducible promoter of sialic acid. Further, the basal expression of pNanA was reduced. These resulted in a versatile dual-functional promoter for EcN that can respond differently to sialic acid depending on the engineered circuitry. The promoter pNanA can function as an inducible promoter or a repressed promoter of sialic acid depending on the presence of NanR. Moreover, nanR can be placed under further inducible or repressible expression to enable an additional layer of control. The construct pEaat-J23113r4-nanR-pNanA-gfp was selected for further characterisation as a sialic acid-based dysbiosis biosensor.

Example 3

Characterisation of Engineered Sialic Acid Biosensor Under Gastrointestinal-Specific Conditions Parental strain of EcN preferentially colonises in the lower gastrointestinal tract specifically the colon and rectum [Sonnenborn, U., & Schulze, *J. Micob. Ecol. Health Dis.* 21: 122-58 (2009); *Schultz, M. Inflamm Bowel Dis.* 14(7): 1012-8 (2008)]. This makes it ideal as a dysbiosis biosensor for the lower gastrointestinal tract. The selected construct was characterised under a series of conditions specific to the lower gastrointestinal tract to assess its suitability.

Figure 7:
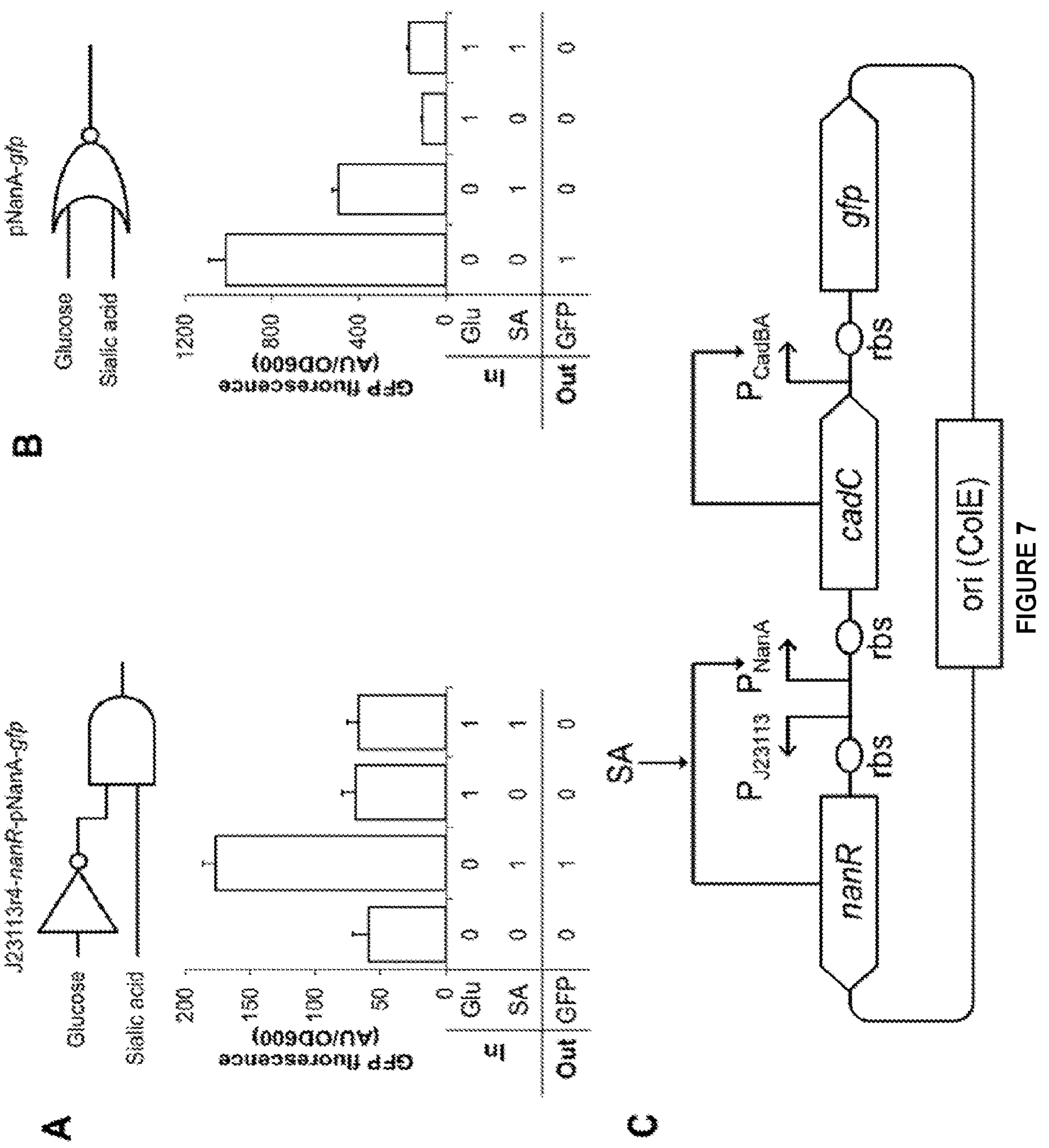
FIG. 7 shows the characterisation of an engineered sialic acid biosensor under gastrointestinal-specific conditions. Responses of A) sialic acid inducible construct (pEaat-J2113r4-nanR-pNanA-gfp) and B) sialic acid repressible construct (pEaat-pNanA-gfp) to induction by sialic acid and glucose combinations. Logic gate diagrams depict the response to sialic acid and glucose as inputs. C) Plasmid design of sialic acid inducible-amplifier construct (pEaat-J2113r4-nanR-pNanA-cadC-pCadBA-gfp). Characterisation of sialic acid inducible construct and sialic acid inducible-amplifier construct in D) LB and E) M9 minimal medium with glycerol. Relative fluorescence expression after 3 and 6 hours of induction shown. F) Characterisation of sialic acid inducible-amplifier constructs under different pH. Relative fluorescence expression after 3 hours of induction shown. G) Growth of EcN with and without sialic acid in M9 minimal medium without carbon source.
Figure 7:
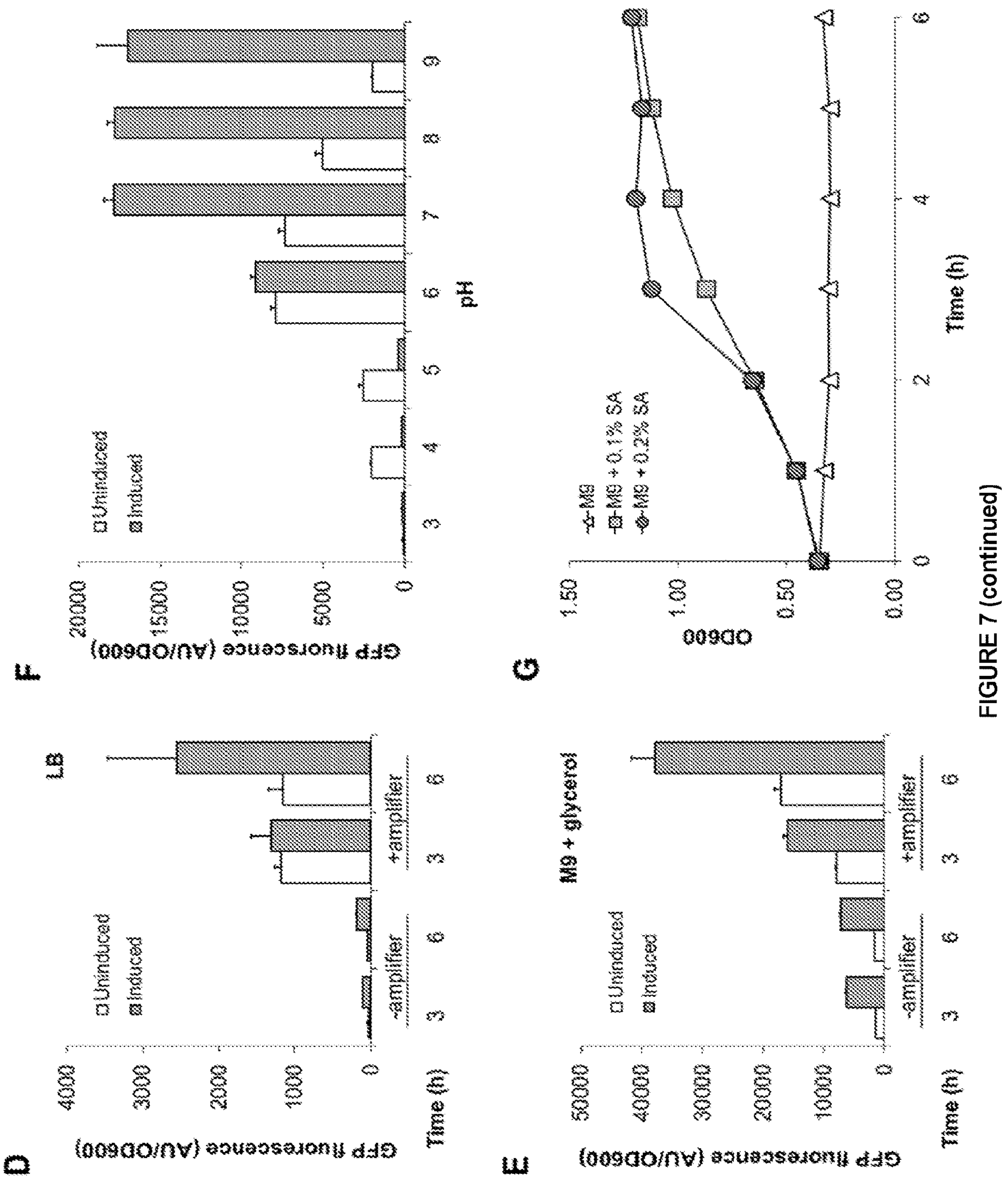

It was noted that pNanA sequence contains a catabolite activator protein (CAP) binding sites at position 4→8. CAP is a transcriptional activator protein that initiates the transcriptional process when bound to cyclic AMP (cAMP). cAMP level is elevated in the absence of glucose, thereby effectively functions as a transcriptional activator for low glucose response. EcN harbouring the inducible (pEaat-J23113r4-nanR-pNanA-gfp) or repressible (pEaat-pNanA-gfp) constructs were subjected to GFP expression characterisation with sialic acid and/or glucose induction. Expectedly, EcN expressing the inducible construct presented a response similar to that of a classical lac operon. GFP expression was repressed in the presence of glucose even when sialic acid was present (FIGS. 7A & 7B). This suggests that NanR might be functionally similar to LacI. Interestingly, EcN expressing the repressible construct responded similarly to glucose, whereby GFP expression is silenced in presence of glucose. These results suggest that transcription of pNanA is driven by cAMP-CAP. The repression of the promoter in the presence of glucose makes it ideal for use in the lower gastrointestinal tract where the level of glucose is expected to be significantly lower. The constructs, both inducible and repressible, are likely to be silenced and non-responsive to sialic acid in upper gastrointestinal tract, and hence their effects will be minimised during the passage through the upper gastrointestinal tract.

Although the trend of pNanA activity in EcN was reversed from a sialic acid repressible promoter to an inducible promoter, it was noted that the induced signal of the inducible construct was significantly lower than even the repressed signal of the repressible construct. The low induced expression level was an issue for the sufficient Cbh expression to deconjugate taurocholate. To overcome this issue, an amplifier module was designed and added to the inducible construct. The gene that encodes for transcriptional activator CadC (SEQ ID NO: 12) was subcloned under pNanA promoter. The promoter pCadBA regulated by CadC was subcloned upstream of gfp (J23113r4-nanR-pNanA-cadC-pCadBA-gfp). Under this design, upon sialic acid induction, expression of CadC under pNanA will in turn activate pCadBA promoter for stronger expression of GFP (FIG. 7C). Here, CadC and pCadBA acts as intermediate transduction module to amplify the signal from pNanA and lead to stronger expression of GFP. Furthermore, CadC was selected due to its responsiveness to external pH as evident from later characterisation (FIG. 7F). The construct was characterised and the induced GFP fluorescence signal was shown to improve significantly. The addition of cadC-pCadBA (SEQ ID NO: 7) into the circuit successfully enabled amplification of signal from the inducible construct (FIG. 7D). However, a temporal lag in GFP expression compared to non-amplifier construct was observed. This could be attributed to the need for intermediate CadC expression, thereby delaying the response, as well as increasing the basal expression level.

The targeted site for the biosensor colonisation is in the lower gastrointestinal tract, where nutrient level of the environment is expected to be poor. All prior characterisation assays were performed in nutrient-rich LB. It is likely that the construct may behave differently in the gut environment where overall nutrition level is different. To determine if the biosensor can function as intended in gastro, the sialic acid inducible (J23113r4-nanR-pNanA-gfp) and sialic acid inducible-amplifier (J23113r4-nanR-pNanA-cadC-pCadBA-gfp) constructs were characterised in M9 minimal medium which functioned as a closer approximation to the gut environment. M9 minimal medium typically contain a carbon source in the form of glucose. As shown previously where glucose interfered with pNanA activity, glycerol was used as the carbon source for M9 minimal medium. Despite the nutrient-poor condition, EcN expressing sialic acid inducible constructs were able to respond as intended to sialic acid induction (FIG. 7E). Further, the temporal response lag previously observed was not as prominent during the characterisation in M9 minimal medium. As previously theorised, pNanA expression could be driven by cAMP-CAP. The lower nutrient content of M9 minimal medium could have resulted in a high level of cAMP, and therefore led to a faster response to sialic acid induction. However, the current result is still inconclusive to verify this proposition. Nonetheless, the results demonstrate that the lower nutrient condition does not adversely affect activity of the inducible constructs.

Another gut environment condition simulated was pH level. The pH level in the gastrointestinal tract is dynamic and differs based on factors including health conditions. The range of pH in healthy subjects was reported to be in the range of 1.6 to 4.2 in the gastric, 6.7 to 7.3 in the small intestine, 5.4 to 6.5 in the cecum, and 6.0 to 7.2 in the colon [Maurer, et al. *PLoS. One.* 10(7): e0129076 doi: 10.1371/journal.pone.0129076 (2015)]. The sialic acid inducible-amplifier construct was characterised in M9 with glycerol medium at pH ranging from 3 to 9. The pH level was observed to influence the activity of the construct (FIG. 7F). No induction activity was observed at low pH from 3 to 5. Surprisingly, instead the expression of GFP was repressed in the presence of sialic acid. The basal expression level increased at pH 6 and subsequently decreased. The cadoperon was reported to be pH sensitive and was activated at pH 5.8 [Watson, N., et al., *J. Bacteriol.* 174(2): 530-40(1992)]. This could have resulted in the basal activity at pH 6 which subsequently decreased at higher pH. The construct was mildly induced from the basal level at pH 6 but strongly induced at high pH from 7 to 9. From the data, the biosensor can be expected to be inactive in gastric due to the low pH environment. Its activity is expected to be higher in the small intestines and colon where pH is between 6.0 and 7.3. Further, it was reported that pH of colon and rectum shift towards basic during *C. difficile* infections with 87% of the CDI patients having stool of more than pH 7 [Gupta, P., et al., *South. Med. J.* 109(2): 91-6 (2016)]. Consistent with the report, a lower pH is associated with a protective effect against *C. difficile* infections [May, T., et al., *Scand. J. Gastroenterol.* 29(10): 916-22 (1994)]. It is unclear whether the pH shift is a result of dysbiosis of the microbiome or a result of pathogen expansion. Nonetheless, the change in pH may enable the biosensor to elicit a stronger response.

It was observed that EcN was able to utilise sialic acid as a carbon source for growth in M9 minimal medium without glycerol (FIG. 7G). The difference in growth rate was not observed in M9 minimal medium containing glycerol. Sialic acid was reported to be utilised by *C. difficile* and pathogenic *E. coli* for expansion during infections [Ng, K. M., et al., *Nat. Lett.* 502: 96-99 (2013); Huang, Y. L., et al., *Nat. Commun.* 6: 8141. doi: 10.1038/ncomms9141 (2015)]. This can enable EcN to double as a nutrient competitor against pathogens for sialic acid in addition to being a biosensor or delivery chassis. Further, the supplementation to EcN growth can amplify the expression of Cbh (SEQ ID NO: 13).

Example 4

Figure 8:
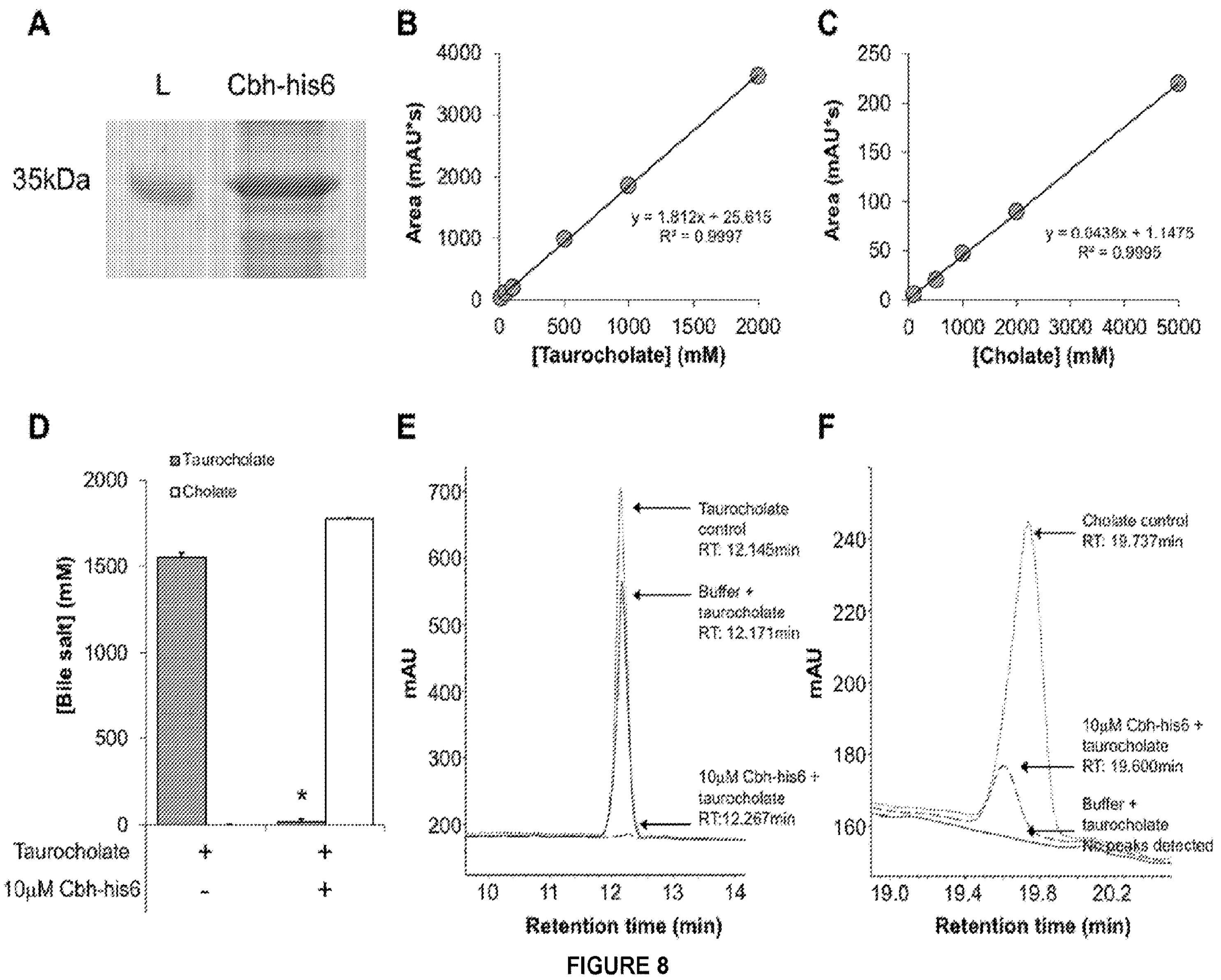
FIG. 8 shows purified Cbh-his6 deconjugates taurocholate into cholate and inhibit *C. difficile* endospore germination. A) 12% SDS-PAGE resolution of purified Cbh-his6 after IMAC and size exclusion chromatography. Expected size of Cbh-his6 is 38 kDa. L represents protein ladder. Standard curves of spectra area against B) taurocholate and C) cholate concentrations from HPLC analysis. D) Concentrations of taurocholate and cholate with and without 3 hours treatment of 10 μM purified Cbh-his6. Student's t-test was performed on taurocholate concentration between treated and untreated. *P<0.005. HPLC spectra of peaks corresponding to elution of E) taurocholate and F) cholate at retention time 12.2-minute and 19.6-minute respectively. G) Germination efficiency of bile salt after treatment with Cbh-his6 based on the CFU enumeration of *C. difficile*. Negative controls of no taurocholate and positive control of no enzyme were performed. Student's t-test was performed between treatment and positive control. *P<0.05. Error bars represent S.E.M of duplicates.
Figure 8:
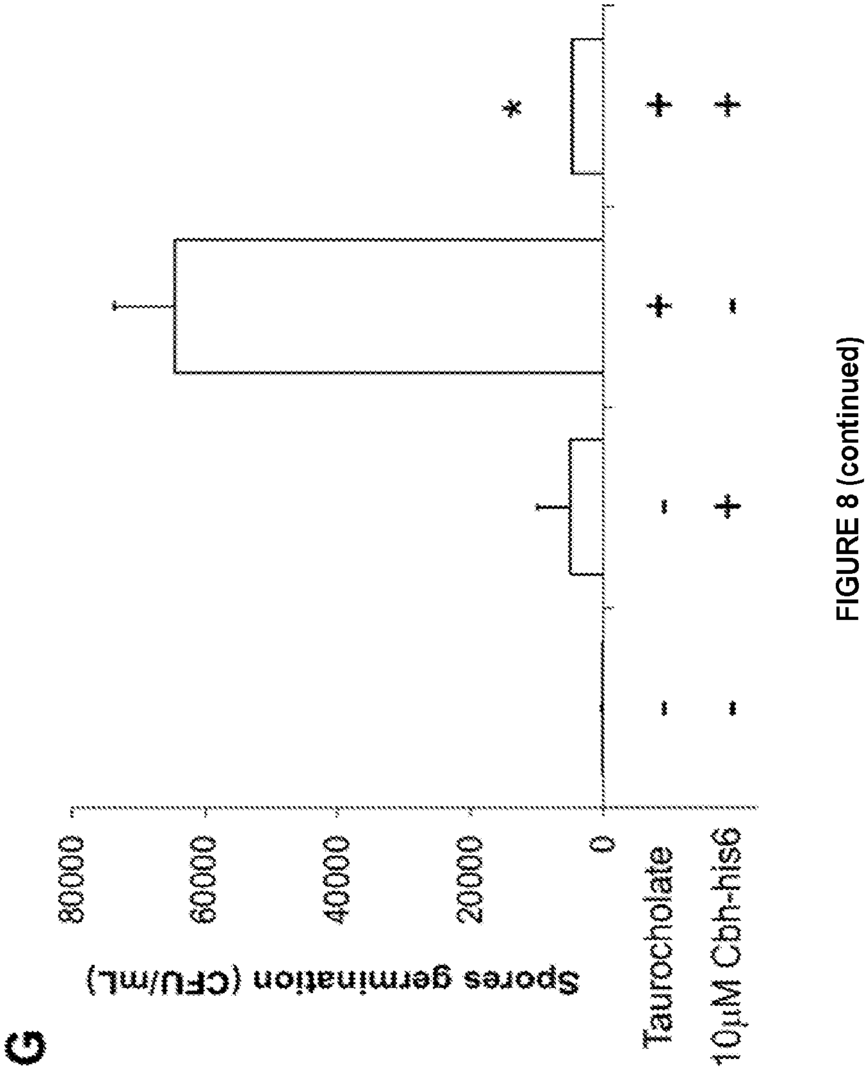

Purified Bile Salt Hydrolase Cbh Deconjugates Taurocholate into Cholate and Inhibits *C. difficile* Endospore Germination The native gene sequence for cbh (SEQ ID NO: 8) was codon-optimised for expression in *E. coli* as well as for compatibility to the BglBrick standard. The codon-optimised sequence is set forth in SEQ ID NO: 9. A C-terminus his6-tag sequence was added and the final gene sequence was subcloned under pBad promoter in pEaat-araC vector. The plasmid was then transformed into *E. coli* strain BL21 for protein expression. Cbh-his6 was induced for expression by L-arabinose and then purified first by IMAC, followed by size exclusion chromatography. Fractions containing Cbh-his6 were then concentrated to 2 mL and yielded a final concentration of 30.66 μM. Proteins with size corresponding to Cbh-his6 can be observed on SDS-PAGE assay of the purified proteins (FIG. 8A).

The activity of Cbh was determined by taurocholate to cholate conversion. HPLC was utilised to determine the concentration of bile salts after enzymatic treatment. HPLC analysis was first run against known concentrations of taurocholate and cholate to determine the retention times and obtain standard curves. Detection of bile salts was performed at 205 nm. Taurocholate was eluted in approximately 12.2-minute runtime, while cholate was eluted in approximately 19.6-minute runtime. The standard curves of taurocholate and cholate were constructed (FIGS. 8B and 8C).

The activity of Cbh was tested against taurocholate by incubating 10 μM of purified Cbh-his6 with 10 mM of taurocholate. Bile salt was extracted and analysed with HPLC. The concentrations of both taurocholate and cholate were determined for the experiment and negative control without Cbh-his6 (FIGS. 8D-8F). No cholate was detected in the negative control. On the other hand, incubation with the protein resulted in a 100-fold decrease in the concentration of taurocholate. Conversely, a high concentration of cholate was detected. A peak corresponding to taurine was not detected within the scope limited by HPLC operating conditions. It can be inferred that heterologous expressed Cbh-his6 retained its native activity to deconjugate taurocholate into cholate. Further, the result showed that approximately 99% of taurocholate was deconjugated within 3 hours of incubation with purified Cbh-his6.

Further reactions of Cbh-his6 with taurocholate were set up with appropriate controls and aliquots were collected. The aliquots were then incubated with purified *C. difficile* endospores. Germination of the endospores were enumerated by CFU counting. Since taurocholate composition was reduced when incubated with Cbh-his6 due to deconjugation into cholate, the germination efficiency from that of the aliquots was expected to reduce. Expectedly, taurocholate incubated with Cbh-his6 showed a 12-fold reduction in endospore germination compared the positive control (FIG. 8G). This result is consistent with the proof-of principle performed on taurocholate and cholate germination efficiency (FIG. 4B). These results supported the proposed strategy for CDI prevention through bile salt composition modulation.

Example 5

Figure 9:
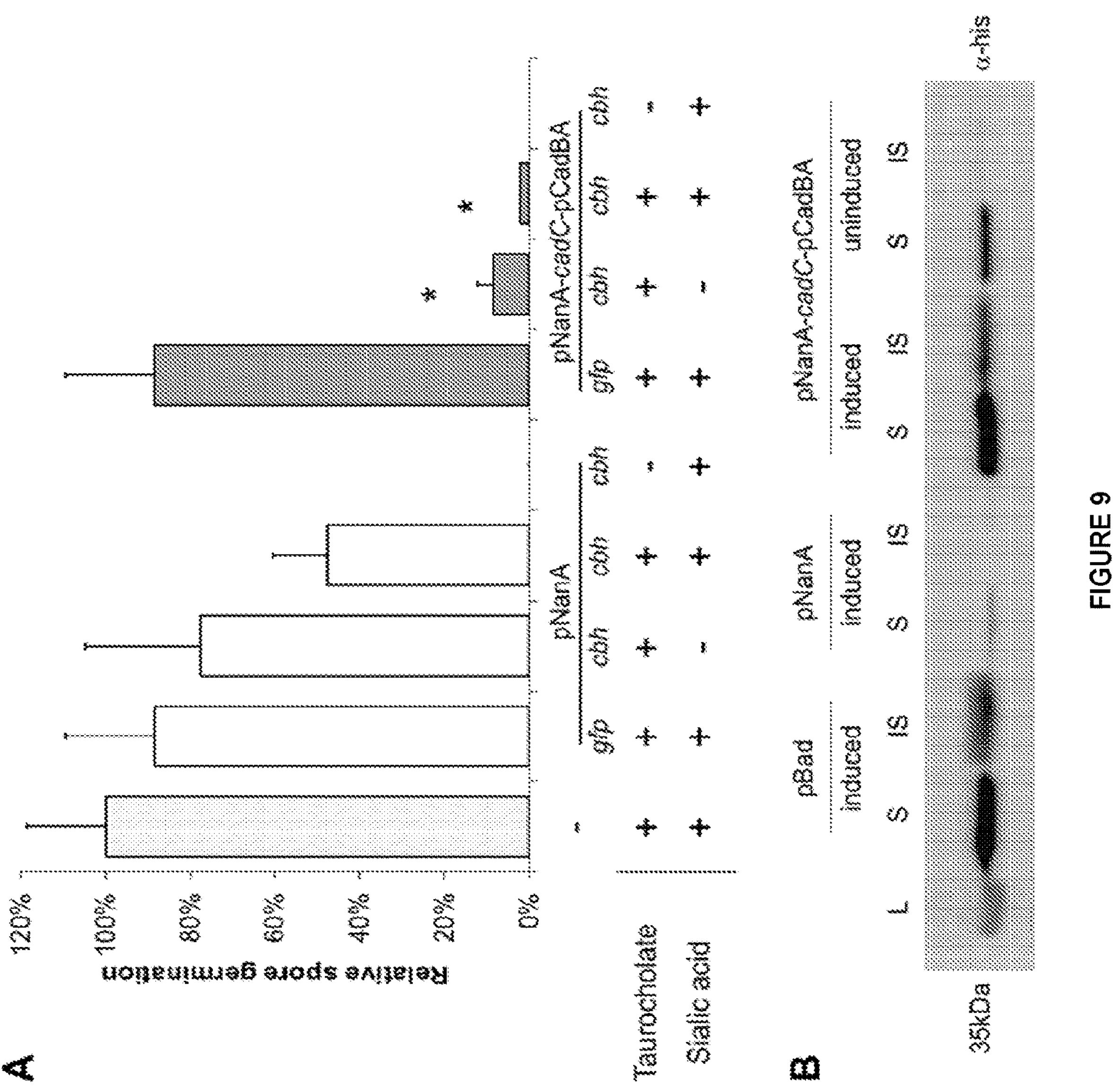
FIG. 9 shows Cbh expression in probiotics inhibits the germination of *C. difficile* endospores. A) Germination efficiency of bile salt after treatment with Cbh-expressing EcN based on the CFU enumeration of *C. difficile*. Two sets of constructs were used, one without (pNanA; blank columns) and one with amplifier module (pNanA-cadC-pCadBA; filled columns). Each set of experiment was performed with gfp expression control, non-induced control, and no-taurocholate negative control. A cell-free positive control (grey column) was performed as well. One-way ANOVA and Student's t-test were performed on amplifier constructs. *P<0.005. Error bars represent S.E.M of duplicates. B) Immunoblot of Cbh-his6 expressed under different promoters from EcN. pBad construct (pEaat-araC-pBad) was induced with 0.2% L-arabinose, pNanA (pEaat-J23113r4-nanR-pNanA) and pNanA-cadC-pCadBA amplifier (pEaat-J23113r4-nanR-pNanA-cadC-pCadBA) constructs were induced by 0.2% sialic acid. Cell densities were adjusted by $OD_{600}$ before protein extraction. L represents protein ladder; S represents soluble fraction; IS represents insoluble fraction. Expected size of Cbh-his6 is 38 kDa. C) Concentrations of taurocholate and cholate after treatment with Cbh-expressing EcN from amplifier construct. Cell-free positive control, gfp expression control, non-induced control, and no-taurocholate negative control were performed. Student's t-test was performed on taurocholate concentration between treated and gfp expression control. *P<0.001.
Figure 9:
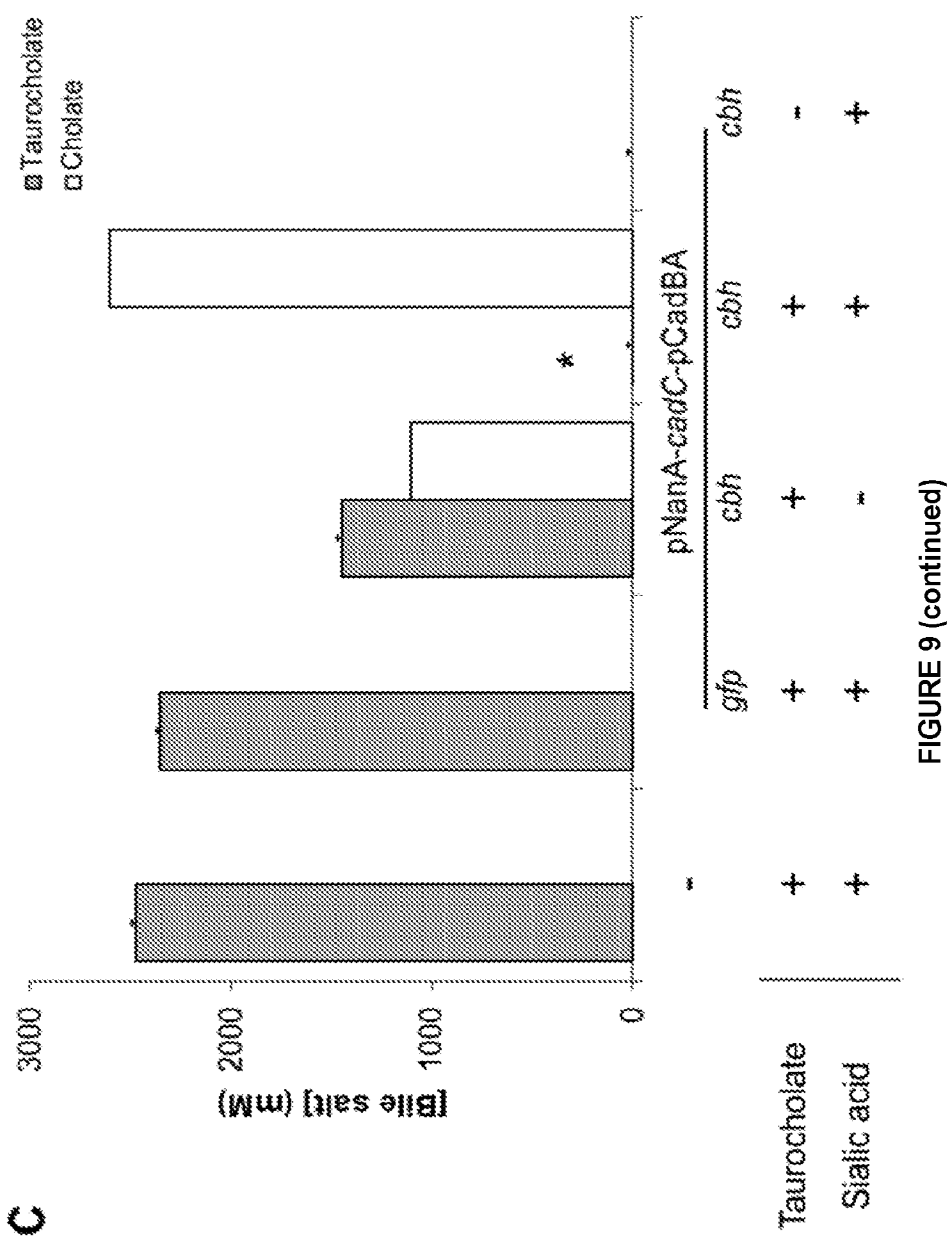

Bile Salt Hydrolase Cbh Expression in Probiotics Inhibits the Germination of *C. difficile* Endospores The gene cbh-his6 was subcloned under pNanA promoter in the sialic acid inducible construct pEaat-J23113r4-nanR-pNanA. The construct expressing gfp in place of cbh functioned as an expression control. The resulting plasmids pEaat-J23113r4-nanR-pNanA-cbh-his6 and pEaat-J23113r4-nanR-pNanA-gfp were transformed into EcN chassis. The strains were incubated with taurocholate and sialic acid. Cell-free positive control, non-induced cbh-his6 expressing strain control, and no-taurocholate cbh-his6 expressing strain negative control were set up as well. Filtered culture medium from each experiment was then collected and tested for *C. difficile* endospore germination efficiency. The EcN strain expressing Cbh-his6 reduced *C. difficile* endospore germination by approximately 1-fold after sialic acid induction compared to the GFP expression negative control (FIG. 9A; blank columns). Although this is a promising result, the fold change is significantly lower in relation to those obtained from purified Cbh-his6. The difference was due to the low expression level of sialic acid-inducible construct. An immunoblot with anti-his antibody was performed and the expression level of Cbh-his6 under pEaat-J23113r4-nanR-pNanA construct was found to be significantly lower than under pEaat-araC-pBad construct (FIG. 9B; lane 2-5). This was in agreement with our dysbiosis sensor characterisation data. To resolve this issue, the CadC amplifier module was designed into the genetic circuit to amplify the inducible expression as previously outlined.

The gene cbh-his6 was subcloned under the amplifier construct pEaat-J23113r4-nanR-pNanA-cadC-pCadBA. Expression of Cbh-his6 in EcN strain was verified by immunoblot (FIG. 9B; lane 6-9). The expression level was amplified, however, it also resulted in a high basal expression level. We then repeated *C. difficile* endospore germination assay with EcN expressing Cbh-his6 or GFP under the new amplifier circuitry. A stark improvement in *C. difficile* endospore germination reduction was observed (FIG. 9A; filled columns). The EcN strain expressing Cbh-his6 was able to reduce *C. difficile* endospore germination by approximately 40-fold after sialic acid induction compared to the expression control. In the absence of sialic acid induction, an approximately 10-fold reduction in endospore germination was achieved. This could be attributed to the strong basal expression of Cbh-his6.

Filtered culture medium from the experiment and controls were also collected for HPLC analysis (FIG. 9C). Taurocholate and cholate concentrations were detected based on previously identified retention time. No cholate was detected in cell-free positive control and GFP expression control, while no taurocholate was detected in induced Cbh-his6 expressing strain. Uninduced Cbh-his6 expressing strain only showed approximately 45% deconjugation of taurocholate in spite of a 10-fold reduction in endospore germination. This suggests that a high accumulation of taurocholate is necessary to achieve effective *C. difficile* endospore germination. Conversely a slight disruption to the build-up of taurocholate can strongly reduce the germination of endospores. These results are consistent with the proof-of-principle germination efficiency assay performed (FIG. 4B). The amplifier construct exhibited a strong basal expression level of Cbh-his6. This basal expression of Cbh-his6 provides a ready-response against any accumulation of taurocholate even in the absence of sialic acid induction.

Example 6

Bile Salt Hydrolase Cbh-Treated *C. difficile* Endospores Exhibit Reduced Exotoxin Secretion and Improve Infection Prognosis of Caco-2 Cells Expression of Cbh in EcN cells was shown to inhibit *C. difficile* endospore germination by modulation of the bile salt conjugation state. The inhibition of endospore germination will in turn delay expansion of vegetative *C. difficile*. In order to determine whether the delayed expansion will represent a difference in pathology of CDI, germinated *C. difficile* were tested against Caco-2 cells, a human colon epithelial cell line isolated from colorectal adenocarcinoma.

As *C. difficile* and Caco-2 were unable to grow in the same laboratory condition, a staggered coculture was performed. This was made possible due to the etiology of CDI being secreted exotoxins [Carter, G. P., et al., *mBio.* 6(3): e00551. doi: 10.1128/mBio.00551-15 (2015)]. Germinated *C. difficile* were first grown in permissible conditions with culture medium collected at regular intervals. The filtered culture medium was then concentrated and buffer-exchanged before incubation with Caco-2 cells. Although this method does not take into account direct interaction between *C. difficile* and Caco-2 cells, it allows secreted toxins from *C. difficile* to be tested against Caco-2 cells.

Figure 10:
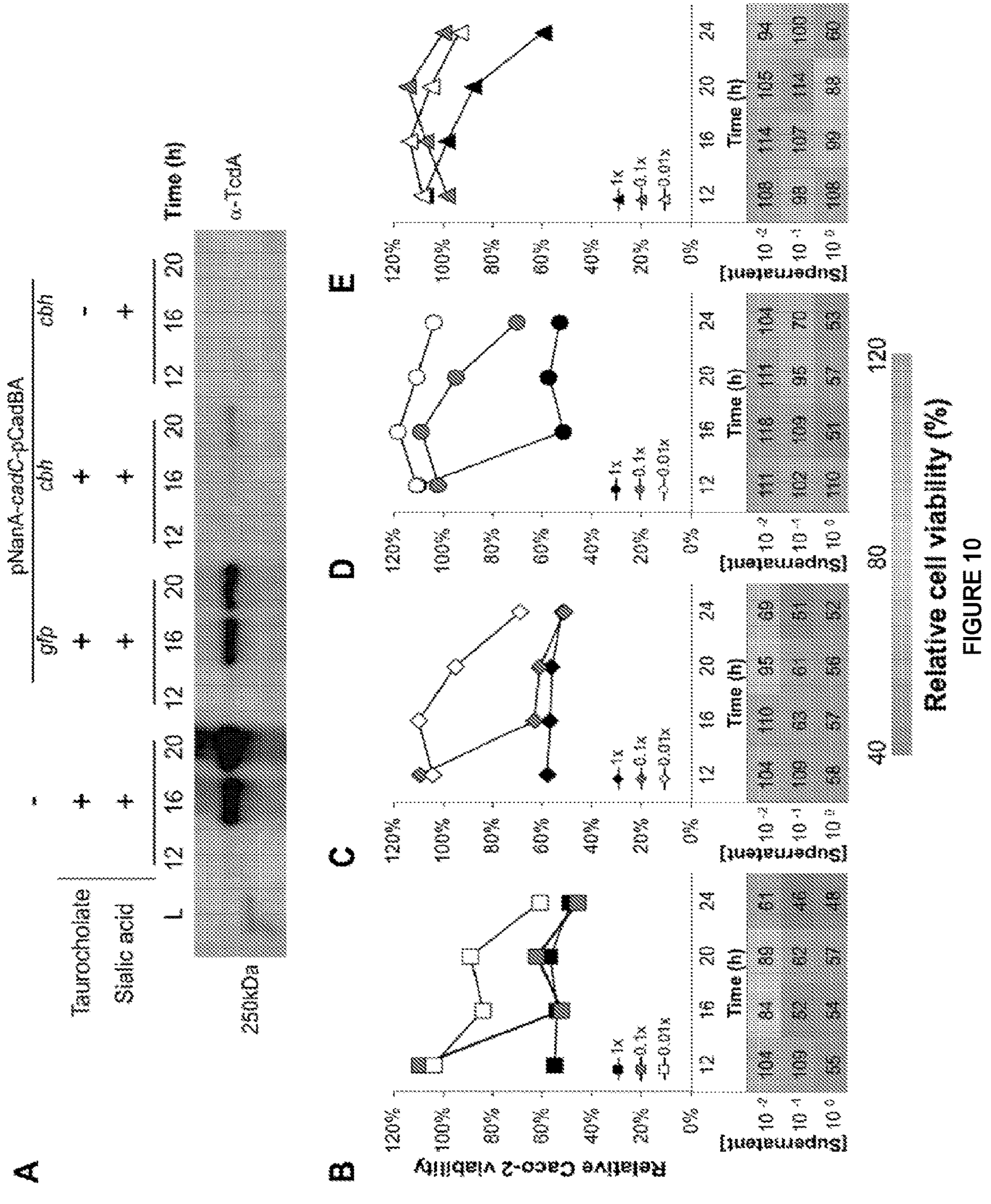
FIG. 10 shows Cbh-treated *C. difficile* endospores exhibit reduced exotoxin secretion and improve infection prognosis of Caco-2 cells. A) Immunoblot of TcdA from 10-times concentrated supernatants collected at respectively time points of germinating *C. difficile* culture. Germinant taurocholate was treated under different conditions before incubation with *C. difficile* endospores. From left, no-cell positive control, gfp expression control, cbh expression treatment, and no-taurocholate negative control. L represents protein ladder. Expected size of TcdA is 308 kDa. Relative cell viability of Caco-2 treated with supernatants collected from germinating *C. difficile* culture under respective conditions, namely B) no-cell positive control, C) gfp expression control, D) cbh expression treatment, and E) no-taurocholate negative control. Supernatants were diluted to final concentration of 1- (filled), 0.1- (grey), and 0.01-fold (blank). Relative cell viability was given by MTT assay normalised to untreated Caco-2 control. Numeric relative cell viability data is shown in matrix. F) Inverted light microscopy photo of Caco-2 cells after 24 hours treatment with respective supernatants to final concentration of 1-fold. tau represents taurocholate; SA represents sialic acid.
Figure 10:
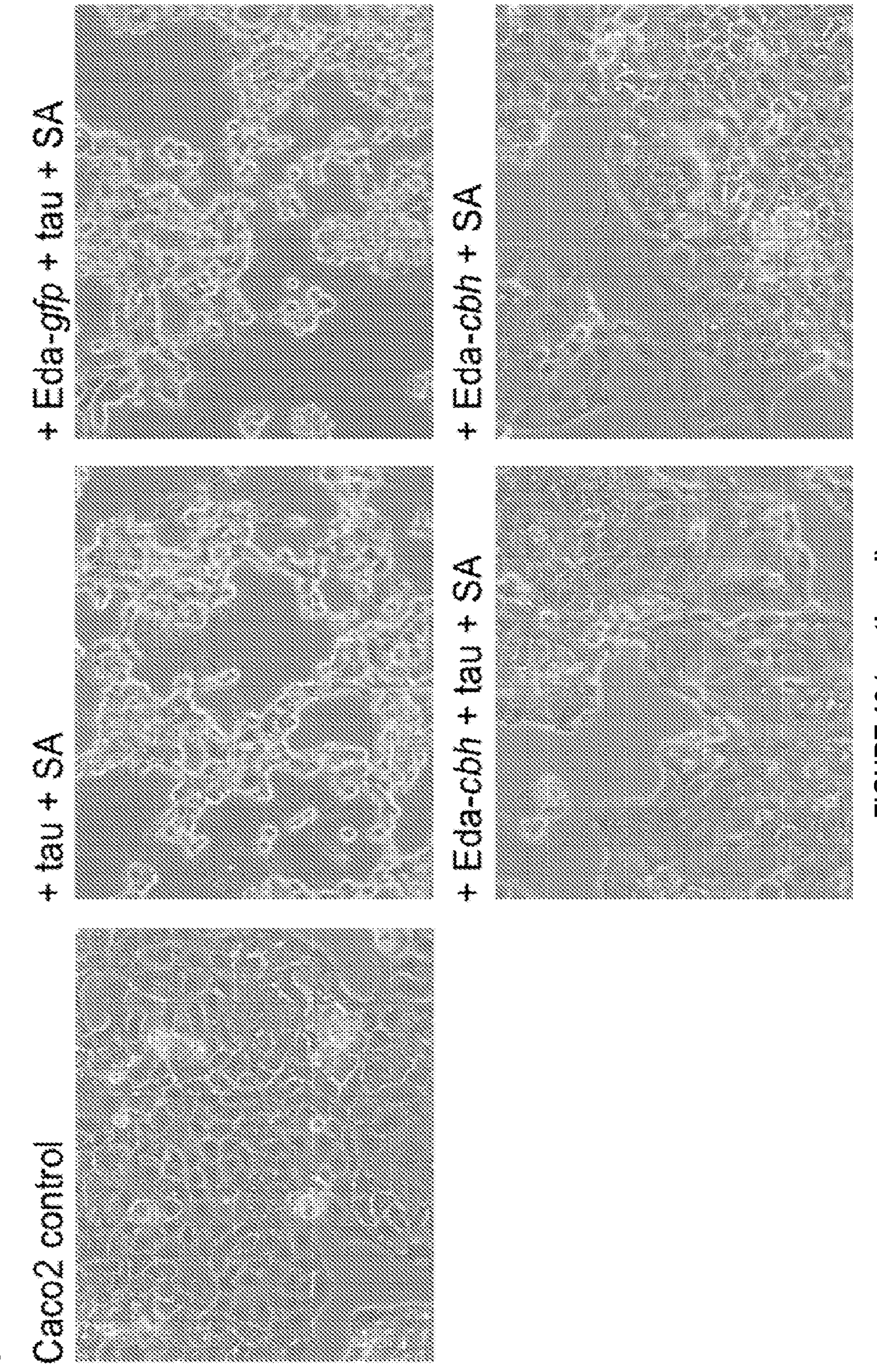

Experiment and controls similar to previous in vitro assay were set up. *C. difficile* endospores were germinated with taurocholate treated by Cbh-expressing EcN (FIG. 10A, lanes 8-10; 10D; 10F bottom left panel), along with cell-free taurocholate positive control (FIG. 10A, lanes 2-4; 10B; 10F top middle panel), GFP-expressing EcN expression control (FIG. 10A, lanes 5-7; 10C; 10F top right panel), or taurocholate-free negative control (FIG. 10A, lanes 11-13; 10E; 10F bottom right panel). Immunoblot was performed on 10-times concentrated filtered supernatants from the experiments collected at regular intervals, and probed for toxin TcdA. Results indicated a reduction in the amount of TcdA secreted into supernatants when treated with Cbh-expressing EcN (FIG. 10A). A time-dependent accumulation of toxins can also be consistently observed. It can be suggested that the inhibition of *C. difficile* endospore germination delayed the growth of vegetative cells and reduced the toxin load secreted into the medium.

Supernatants were collected at regular intervals following *C. difficile* induction for germination. The supernatants were concentrated and then serial diluted to 1- to 0.01-fold when incubated with Caco-2 cells. The cell viabilities of Caco-2 were assayed with MTT following 48 hours incubation. Expectedly, Caco-2 incubated with supernatant collected from Cbh-expressing EcN treated *C. difficile* showed higher final cell viability compared to those of expression control (FIGS. 10B-10E). This is consistent with the amount of TcdA in the supernatants. Further, the cell morphology of Caco-2 was observed to be different between treatment with the supernatants from Cbh-expressing EcN and expression control (FIG. 10F). Caco-2 treated with supernatant from Cbh-expressing EcN showed morphology close to untreated Caco-2. On the other hand, treatment with supernatant from expression control result in similar morphology as treatment with supernatant from positive control. The Caco-2 cells showed detachment from the culture plates and shriveled cell shape associated with cell death.

Overall, the assays showed that Cbh-expressing EcN can improve prognosis of ex vivo Caco-2 cell culture. Cbh expressed from EcN can deconjugate taurocholate into cholate, resulting in reduced germination of *C. difficile* endospores. The delay in germination affected the secretion of exotoxins into culture medium, and this in turn resulted in improvement in Caco-2 infection prognosis. It was noted TcdA continued to be secreted into supernatant from Cbh treatment and not entirely inhibited. This is consistent with the in vitro assay, a small *C. difficile* germination even after treatment with engineered EcN (FIG. 9A). These vegetative cells proliferated in the culture medium leading to secretion of TcdA. It is possible that the exotoxins may accumulate even after treatment with engineered EcN. However, the nutrient-poor environment in vivo may limit the proliferation of *C. difficile*, and initial germination of cells has a greater effect on the overall virulence load than proliferation that follows. The extent of these dynamics will need to be further elucidated in vivo to determine the effectiveness of the treatment. Nonetheless, it is conclusive that the treatment of *C. difficile* endospores with engineered EcN results in a reduced amount of exotoxins secreted. This in turn improved Caco-2 cell viability compared to the expression control.

Example 7

Figure 11:
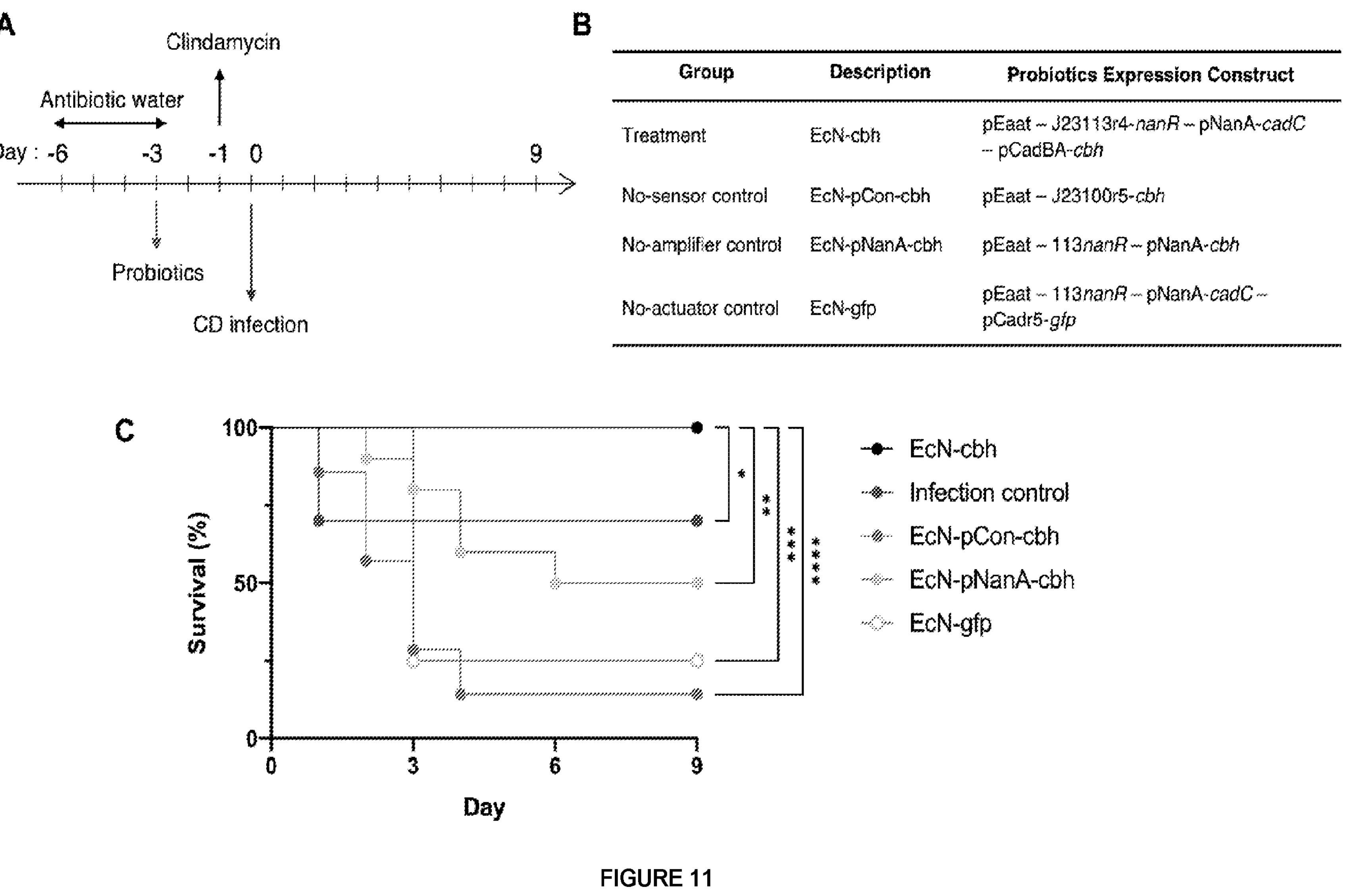
FIG. 11 shows efficacy of Cbh-expressing EcN in treatment of murine CDI models infected with *C. difficile*. A) Experimental timeline of infection assay showing point of administration for treatment, probiotics, and *C. difficile*. B) Table of experimental groups and expression constructs of engineered probiotics given. C) Survival curve and D) mean weight of respective groups following infection with *C. difficile* cells over nine days. Gehan-Breslow-Wilcoxon test was performed between treatment and control groups. *P<0.05, P<0.01, *P<0.001, ****P<0.0001. E) Maximum clinical sickness score (CSS) exhibited by respective mice within each group following infection with *C. difficile* cells over six days. Unpaired student's t-test was performed between treatment and control groups. P<0.01, *P<0.001.
Figure 11:
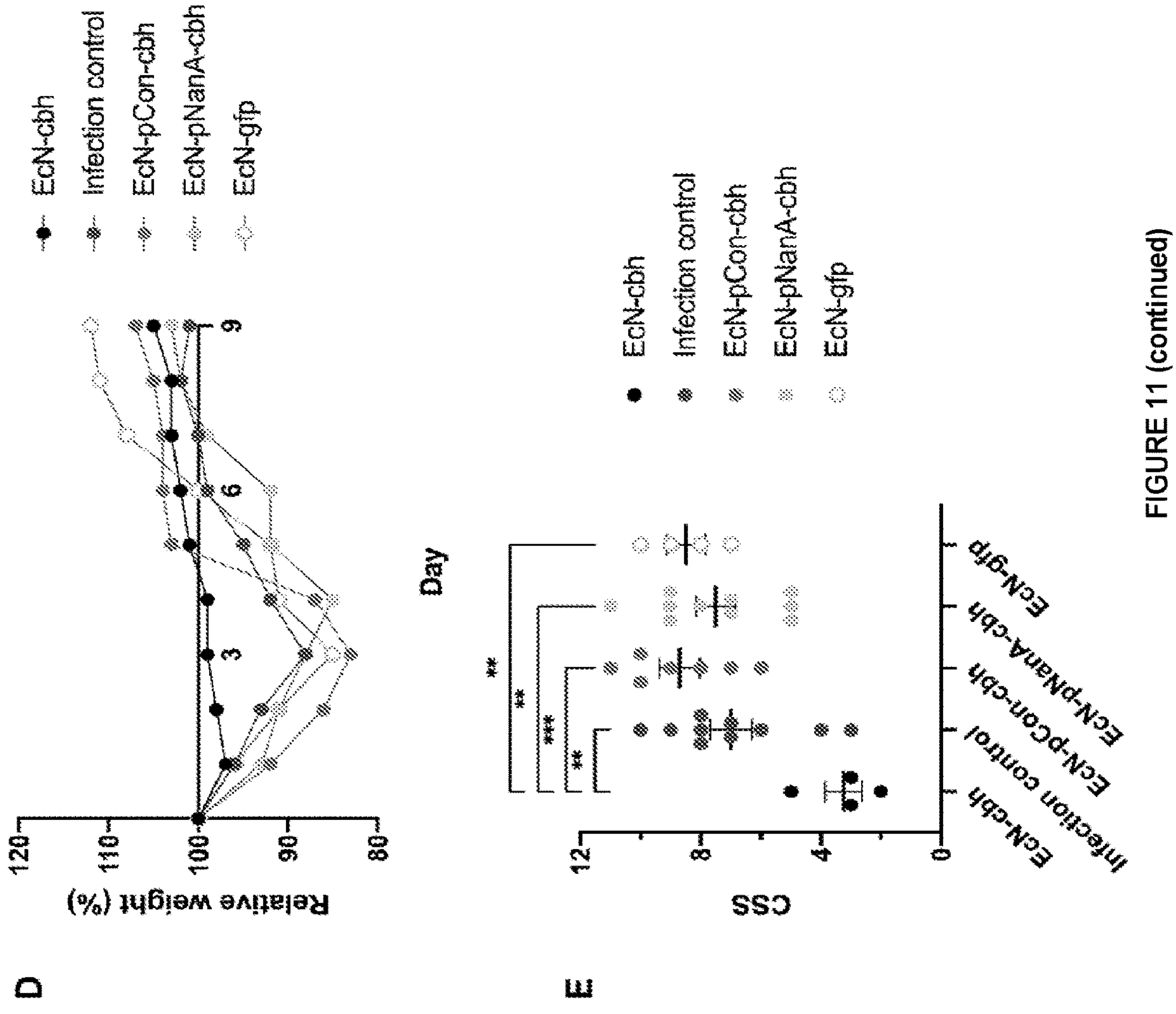

Pre-Treatment with Engineered Probiotics Expressing Dysbiosis Sensor-Controlled Bile Salt Hydrolase Cbh Provided Protection Against Infection from *C. difficile* in Murine Model Murine model of CDI had previously been demonstrated [Chen, X., et al., *Gastroenterology.* 135: 1984-1992 (2008)]. This model was adapted and modified in this study to test the efficacy of the engineered EcN (FIG. 11A). Briefly, the mice were given a dose of engineered probiotics (treatment or control groups) or blank (infection control group) 3 days prior to infection (day −3). Infection by *C. difficile* (107 CFU) was performed on day 0. Mortality, weight, and clinical symptoms of the mice were then recorded over the course of 9 days. The clinical symptoms were then scored and tabulated according to previously established standards [Shelby, R. D., et al., *Int. J. Surg*. doi: 10.1080/08941939.2019.1571129 (2019)].

The treatment group ('EcN-cbh') was given probiotics harbouring the Cbh-expressing construct (pEaat-J23113r4-nanR-pNanA-cadC-pCadBA-cbh). This construct consists of multiple genetic modules namely, sensor, amplifier, and actuator. In order to adequately demonstrate the efficacy of the fully engineered probiotics, various control probiotics were generated to comprise constructs that lack one of each genetic module. The probiotics generated for these control groups are summarised in FIG. 11B. No-sensor control group ('EcN-pCon-cbh') was given engineered probiotics that constitutively express Cbh without dysbiosis sensor. No-amplifier control group ('EcN-pNanA-cbh') was given engineered probiotics that lack amplifier module. No-actuator control group ('EcN-gfp) was given engineered probiotics that express GFP in place of Cbh. All probiotics were administrated in a single dose of $10^9$ CFU on day −3, and infection control was given sucrose in place of engineered probiotics.

Mice were infected with 107 CFU of *C. difficile* on day 0 of the assay (FIG. 11A). Survival of the treatment group performed significantly better than all control groups. 100% of mice survived the infection (FIG. 11C) compared to infection control (70.0%; P=0.0461), no-sensor control (14.3%; P<0.0001), no-amplifier control (50.0%; P=0.0063), and no-actuator control (25.0%; P=0.0005). Infected mice displayed severe symptoms between day 2 to day 4. The relative weight of treatment group during this period was comparatively more stable to all control groups which showed relative weight loss of more than 10% (FIG.

11D). Each mouse was also assigned a clinical sickness score (CSS) ranging from 0 to 12 daily from day 0 to 6. The CSS is assigned according to three criteria; stool, behaviour, and weight loss [Shelby, R. D., et al., *Int. J. Surg*. doi: 10.1080/08941939.2019.1571129 (2019)]. Based on CSS, the severity of the infection can be described as normal (0 to 2), mild (3 to 5), moderate (6 to 8) and severe (9 to 12). The CSS scored by each mouse was then used to tabulate the mean score of the group (FIG. 11D). Treatment group scored the lowest CSS compared to all groups with a mean of 3.3. This score is significantly lower compared to infection control group (7.0; P=0.0075), no-sensor control group (8.7; P=0.0005), no-amplifier control group (7.5; P=0.0026), and no-actuator control group (8.5; P=0.0011). Taken together, these results demonstrate that the administration of engineered probiotics prior to *C. difficile* infection was able to confer prophylactic protection that improve infection prognosis through lowering mortality and reducing severity of symptoms.

Further, the results showed that constitutive expression of Cbh in the no-sensor group did not improve survival of mice compared to the no-actuator control (P=0.247). Conversely, the expression of Cbh from dysbiosis sensor in the no-amplifier group showed an improvement in survival over the no-sensor group (P=0.0305). This is in spite of expression level of Cbh from constitutive promoter being higher than that from pNanA promoter in vitro. The outcomes of the various control groups suggest that the dysbiosis sensing module that drives on-demand in vivo expression of Cbh is necessary in achieving the intended function of modulating *C. difficile* infection. The nutrient level in lower gastrointestinal tract is expected to be poorer, and inefficient allocation of nutrient towards continuous expression of enzymes might have worked against the no-sensor probiotics. The result highlights the importance of the dysbiosis sensor in controlling the expression of Cbh from engineered probiotics to achieve high activity against CDI in vivo.

Taken together, these results demonstrate that engineered probiotics expressing dysbiosis sensor-controlled bile salt hydrolase Cbh are able to provide prophylactic resistance against *C. difficile* infection. Both the restoration of bile salt metabolism and the dysbiosis-sensing module were demonstrated to be critical in providing protection against infection. Taken together, the probiotics demonstrated high efficacy as prophylaxis against infection of *C. difficile*.

Example 8

Expression of the Genetic Circuit in Other Probiotic Strains to Achieve Similar Therapeutic Functions The genetic circuit in this invention can be easily expressed in other probiotic species, both of gram negative and gram positive. Many species of native probiotics can be engineered as live biotherapeutics [O'Toole, P. W., Marchesi, J. R., & Hill, C. Nat. *Microbiol.* 2: 17057. doi: 10.1038/nmicrobiol.2017.57 (2017)]. Examples of such species include, but are not limited to, *Bacteroides* sp., *Clostridium* sp., *Faecalibacterium* sp., *Lactococcus lactis*, and *Lactocbacillus* sp. This invention addresses difficult technical issues of enzymatic expression and response to dysbiosis. The expression can be grafted onto other probiotic species to achieve similar therapeutic functions. This can enable the engineered probiotics to colonise and target other locations of the gastrointestinal tract such as the duodenum, jejunum or ileum.

Example 9

The Antibiotic Selection-Free Probiotic Chassis can be Applied to Deliver Other Genetic Circuits In Situ An antibiotic selection-free probiotic chassis was engineered through the generation of auxotrophic phenotype in *E. coli* Nissle strain. This chassis is accompanied by a plasmid consisting of alanine racemase gene as selection marker. This chassis enables the delivery of engineered genetic circuit in situ and can be utilised for other purposes such as, but not limited to, pathogen targeting, cancer targeting, and metabolites/biologic synthesis and delivery.

Example 10

The Sialic Acid-Based Sensor Functions as a Proxy to Dysbiosis and can be Applied to Other Dysbiosis-Associated Diseases and Infections This invention responds to a dysbiosis event based on a sialic acid-responsive promoter. The sialic acid-responsive promoter can be engineered to respond to either upregulation or downregulation of sialic acid. Dysbiosis of the microbiome is also associated with a number of other diseases such as, but not limited to, inflammatory bowel disease, pathogenic infections, type-2 diabetes mellitus, asthma, obesity, autism, and rheumatoid arthritis [Packey, C., D., & Sartor, R. B. *Curr. Opin. Infect. Dis.* 22(3): 292-301 (2009)]. The sialic acid-based sensor can be applied to engineered biotherapeutics that target such diseases.

Example 11

The Genetic Circuit can be Optimised and Integrated into EcN Genome to Confer Further Stability In this invention, the genetic circuit is expressed on plasmids. Alternatively, the genetic circuit can be integrated into the genome for further stability. This will avoid unnecessary but potential horizontal gene transfer to the microbiome. Multiple sites of integration have been identified in the EcN genome [Isabella, V. M., et al., *Nat. Biotech.* 36: 857-864 (2018)]. Integration of this genetic circuit can be performed at these sites without disrupting the genome stability of the probiotic strain, whilst resisting spontaneous loss or inactivation of the integrated genetic circuit.

Summary

Engineered Probiotic Chassis EcN

An embodiment of the invention provides *E. coli* Nissle with two alanine racemase genes deleted from the genome, which is able to maintain plasmids containing an alanine racemase gene as selection marker for an extended period without additional selection. This avoids unnecessary exposure of antibiotic resistance genes to the microbiome. EcN can then be co-administered with *C. difficile*-targeting antibiotics regimens to colonise the gastrointestinal tract and exert antimicrobial activity against *C. difficile*. The engineered probiotic can remain in the GI tract for an extended period, enabling prophylactic applications.

Sialic Acid Inducible System

In an embodiment of the invention, a sialic acid inducible system is provided which consists of a genetic circuit including pNanA promoter and optional NanR transcription factor, CadC transcriptional factor and its promoter pCadBA. NanR reverses the inducibility of pNanA and CadC-pCadBA amplifies the overall expression level. This system responds to changes in sialic acid depending on the parts used in the system. Elevated sialic acid levels are associated with dysbiosis of the gastrointestinal microbiome, so the system provides a timely response to dysbiosis events through the expression of therapeutic proteins limited to the occurrence of the dysbiosis event.

CadC Amplification System

In an embodiment of the invention, the element CadC protein and pCadBA promoter are provided to amplify expression from the sialic acid-responsive promoter through an intermediate transcription activator expression. The primary function is to amplify expression of bile salt hydrolase to a therapeutically significant level. A secondary function is to enable the genetic circuit to be sensitive to pH; which provides an additional layer of control to bile salt hydrolase expression.

Bile Salt Hydrolase Expression

Bile salt hydrolase is expressed to catalyse the deconjugation of taurocholate into cholate in order to reduce the endospore germination efficiency of *C. difficile* caused by the elevated bile salt during dysbiosis, an event that precedes CDIs. The enzyme inhibits germination of endospores and leads to an overall reduction of toxins secreted by *C. difficile*.

By expressing bile salt hydrolase preemptively in response to dysbiosis, the probiotic is able to function as an autonomous prophylaxis against CDIs. This strategy will be effective against the prevention of rCDIs as well. Hence, this probiotic address a gap in CDI management and can be targeted at patients who are at risk of CDIs and rCDIs.

An advantage of the invention is that it provides a non-bactericidal approach to controlling CDI and rCDI; thereby avoiding resistance towards this method.

REFERENCES

Any listing or discussion of an apparently prior-published document in this specification should not necessarily be taken as an acknowledgement that such document is part of the state of the art or is common general knowledge.

Begley, M., Gahan, C. G. M, & Hill, C. (2005) The interaction between bacteria and bile. *FEMS. Microbiol. Rev.* 25: 625-51.

Buffie, C. G., Bucci, V., Stein, R. R., McKenny, P. T., Ling, L., Gobourne, A., et al. (2015) Precision microbiome reconstitution restores bile acid mediated resistance to *Clostridium difficile. Nat. Lett.* 517: 205-8.

Carter, G. P., Chakravorty, A., Pham Nguyen, T. A., Mileto, S., Schreiber, F., Li, L., et al. (2015) Defining the roles of TcdA and TcdB in localised gastrointestinal disease, systemic organ damage, and the host response during *Clostridium difficile* infections. mBio. 6(3): e00551. doi: 10.1128/mBio.00551-15.

Chen, X., Katchar, K., Goldsmith, J. D., Nanthakumar, N., Chekins, A., Gerding, D. N., et al. (2008) A mouse model of *Clostridium difficile*-associated disease. *Gastroenterology.* 135: 1984-1992.

Chilton, C. H., Pickering, D. S., & Freeman, J. (2018) Microbiological factors affecting *Clostridium difficile* recurrence. *Clin. Microbiol. Infect*. Published ahead of print. doi: 10.1016/j.cmi.2017.11.017.

Coleman, J. P., & Hudson, L. L. (1995) Cloning and characterization of a conjugated bile acid hydrolase gene from *Clostridium perfringens. Appl. Environ. Microbiol.* 61(7): 2514-20.

Gebhart, D., Lok, S., Clare, S., Tomas, M., Stares, M., Scholl, D., et al. (2015) A modified R-type bacteriocin specifically targeting *Clostridium difficile* prevents colonization of mice without affecting gut microbiota diversity. *mBio.* 6(2): doi: 10.1128/mBio.02368-14

Gupta, P., Yakubov, S., Tin, K., Zea, D., Garankina, O., Ghitan, M., et al (2016) Does alkaline colonic pH predispose to *Clostridium difficile* infection? *South. Med. J.* 109(2): 91-6.

Huang, Y. L., Chassard, C., Hausmann, M., von Itzstein, M., & Hennet, T. (2015) Sialic acid catabolism drives intestinal inflammation and microbial dysbiosis in mice. *Nat. Commun.* 6: 8141. doi: 10.1038/ncomms9141.

Hwang, I, Y., Koh, E., Wong, A., March, J. C., Bentley, W. E., Lee, Y. S., & Chang, M. W. (2017) Engineered probiotic *Escherichia coli* can eliminate and prevent *Pseudomonas aeruginosa* gut infection in animal models. *Nat. Commun.* 8: 15028. doi: 10.1038/ncomms15028.

Isabella, V. M., Ha, B. H., Castillo, M. J., Lubkowicz, D. J., Rowe, S. E., Anderson, C. L., et al. (2018) Development of a synthetic live bacterial therapeutic for the human metabolic disease phenylketonuria. *Nat. Biotech.* 36: 857-864.

Kalivoda, K. A., Steenbergen, S. M., Vimr, E. R., & Plumbridge, J. (2003) Regulation of sialic acid catabolism by the DNA binding protein NanR in *Escherichia coli. J. Bacteriol.* 185(16): 4806-15.

Keseler, I. M. Mackie, A., Peralta-Gil, M., Santos-Zavaleta, A., Gama-Castro, S., Bonavides-Martinez, C., et al. (2013) EcoCyc: fusing model organism databases with synthetic biology. *Nuc. Acids. Res.* 41: 605-12.

Maurer, J. M., Schellekens, R. C. A., van Rieke, H. M., Wanke, C., Iordanov, V., Stellaard, F., et al. (2015) Gastrointestinal pH and transit time profiling in healthy volunteers using the IntelliCap system confirms ileo-colonic release of ColoPulse tablets. *PLoS. One.* 10(7): e0129076 doi: 10.1371/journal.pone.0129076

May, T., Mackie. R. I., Fahey Jr, G. C., Cermin, J. C., & Garleb, K. A. (1994) Effect of fiber source on short-chain fatty acid production and on the growth and toxin production by *Clostridium difficile. Scand. J. Gastroenterol.* 29(10): 916-22.

Nelson, R. (2007) Antibiotic treatment for *Clostridium difficile*-associated diarrhea in adults. *Cochrane. Database. Syst. Rev.* 18(3): CD004610.

Ng, K. M., Ferreyra, J. A., Higginbottom, S. K., Lynch, J., Kashyap, P. C., Gopinath, S., et al. (2013) Microbiota-liberated host sugars facilitate post antibiotic expansion of enteric pathogens. *Nat. Lett.* 502: 96-99.

O'Toole, P. W., Marchesi, J. R., & Hill, C. (2017) Next-generation probiotic: the spectrum from probiotics to live biotherapeutics. *Nat. Microbiol.* 2: 17057. doi: 10.1038/nmicrobiol.2017.57.

Packey, C., D., & Sartor, R. B. (2009) Commensal bacteria, traditional and opportunistic pathogens, dysbiosis and bacterial killing in inflammatory bowel diseases. *Curr. Opin. Infect. Dis.* 22(3): 292-301.

Petrosillo, N. (2018) Tackling the recurrence of *Clostridium difficile* infections. *Med. Mal. Infect.* 48(1): 18-22.

Ridlon, J. M., Kang, D., & Hylemon, P. B. (2006) Bile salt biotransformation by human intestinal bacteria. *J. Lipid. Res.* 47: 241-59

Ridlon, J. M., & Hylemon, P. B. (2012) Identification and characterization of two bile acid coenzyme A transferases from *Clostridium scindens*, a bile acid 7 α-dehydroxylating intestinal bacterium. *J. Lipid. Res.* 53: 66-76.

Roberts, A. P., & Mullany, P. (2010) *Clostridium difficile*: no longer an enigmatic pathogen? *Clostridium difficile*: methods and protocols. Ed: P. Mullany, A. Roberts. Springer US, New York. 3-8

Schultz, M. (2008) Clinical use of *E. coli* Nissle 1917 in inflammatory bowel disease. *Inflamm Bowel Dis.* 14(7): 1012-8.

Shelby, R. D., Tengberg, N., Conces, M., Olson, J. K., Navarro, J. B., Bailey, M. T., et al. (2019) Development of a standardized scoring system to assess a murine model of *Clostridium difficile* colitis. *Int. J. Surg*. doi: 10.1080/08941939.2019.1571129.

Sonnenborn, U., & Schulze, J. (2009) The non-pathogenic *Escherichia coli* strain Nissle 1917—features of a versatile probiotic. *Micob. Ecol. Health Dis.* 21: 122-58.

Sorg, J. A., & Soenenshein, A. L. (2008) Bile salts and glycine as cogerminants for *Clostridium difficile* spores. *J. Bacteriol.* 190(7): 2505-12.

Watson, N., Dunyak, D. S., Rosey, E. L., Slonczewski, J. L., & Olson, E. R. (1992) Identification of elements involved in transcriptional regulation of the *Escherichia coli* cad operon by external pH. *J. Bacteriol.* 174(2): 530-40.

The invention claimed is:

1. An expression cassette comprising;

i. a bile salt hydrolase gene, ii. a sialic acid-responsive promoter for N-acetylneuraminate lyase (pNanA), operably linked to the bile salt hydrolase gene, iii. a pNanA repressor consisting of a N-acetylneuraminate repressor (NanR) protein-encoding polynucleotide operably linked to a constitutive promoter, and iv. an activator and promoter to increase the expression of the bile salt hydrolase gene, wherein the activator is a CadC protein (Cadmium resistance transcriptional regulatory protein)-encoding polynucleotide positioned downstream and under the control of pNanA, and the promoter is pCadBA (a promoter of lysine: cadaverine antiporter & lysine decarboxylase 1 genes) positioned downstream of the CadC protein-encoding polynucleotide and operably linked to the bile salt hydrolase gene.

2. The expression cassette according to claim 1, wherein the bile salt hydrolase gene is a choloylglycine hydrolase (Cbh) protein-encoding polynucleotide from *Clostridium perfringens*.

3. The expression cassette according to claim 2, wherein the Cbh protein-encoding polynucleotide comprises a nucleic acid sequence that has at least 80% sequence identity to the nucleic acid sequence set forth in SEQ ID NO: 8 or SEQ ID NO: 9.

4. The expression cassette according to claim 1, wherein pNanA is from *E.coli*.

5. The expression cassette according to claim 4, wherein the NanR protein-encoding polynucleotide is positioned upstream of pNanA.

6. The expression cassette according to claim 5, wherein the NanR protein-encoding polynucleotide comprises the nucleic acid sequence set forth in SEQ ID NO: 5.

7. The expression cassette according to claim 1, wherein the constitutive promoter is selected from the group consisting of pBad, promoter of araBAD structural genes, with a polynucleotide encoding AraC, Arabinose operon regulatory protein J23108; and J23113 with rbs 4, wherein the rbs 4 consists of the nucleotide sequence set forth in positions 944-954 of SEQ ID NO: 6; and wherein the araBAD structural genes are genes of ribulokinase, L-arabinose isomerase and L-ribulose-5-phosphate 4-epimerase.

8. The expression cassette according to claim 7, wherein the constitutive promoter operably linked to the NanR protein-encoding polynucleotide is J23113-rbs4.

9. The expression cassette according to claim 8, wherein the cassette comprises J23113-rbs4-NanR consisting of the nucleic acid sequence set forth in SEQ ID NO: 6.

10. The expression cassette according to claim 1, wherein the activator CadC protein-encoding polynucleotide and promoter pCadBA nucleic acid sequences are set forth in SEQ ID NO: 7.

11. The expression cassette according to claim 1, wherein the cassette is comprised in one or more plasmid vectors.

12. The expression cassette according to claim 11, wherein the plasmid vector is pEaat.

13. The expression cassette according to claim 2, wherein the bile salt hydrolase gene is codon-optimized for expression in a probiotic cell, wherein the probiotic cell is selected from the group consisting of *E. coli, Bacteroides* sp., *Clostridium* sp., *Faecalibacterium* sp., *Lactococcus lactis*, and *Lactobacillus* sp.

14. The expression cassette of claim 2, wherein the choloylglycine hydrolase (Cbh)protein-encoding polynucleotide encodes the amino acid sequence set forth in SEQ ID NO: 13.

15. The expression cassette of claim 4, wherein the pNanA comprises the nucleic acid sequence set forth in SEQ ID NO: 4.

16. The expression cassette of claim 5, wherein the NanR protein-encoding polynucleotide encodes the amino acid sequence set forth in SEQ ID NO: 11.

17. The expression cassette of claim 12, wherein the plasmid vector pEaat consists of the nucleic acid sequence set forth in SEQ ID NO: 1.

18. The expression cassette of claim 13, wherein the bile salt hydrolase gene polynucleotide sequence is codon-optimized for expression in the probiotic cell and consists of the nucleic acid sequence set forth in SEQ ID NO: 9.

19. A composition comprising:

a) a probiotic bacterium; and b) an expression cassette of claim 1, wherein the probiotic bacterium comprises the expression cassette for production of bile salt hydrolase.

20. The composition of claim 19, wherein the probiotic bacterium is selected from the group consisting of *E. coli, Bacteroides* sp., *Clostridium* sp., *Faecalibacterium* sp., *Lactococcus lactis*, and *Lactobacillus* sp.

21. The composition of claim 19, wherein the probiotic bacterium is auxotrophic.

22. The composition of claim 21, wherein the auxotrophic bacterium has had Alanine racemase genes deleted and cannot divide in the absence of D-Alanine.

23. The composition of claim 19, wherein the composition is for prophylaxis or treatment of *C. difficile* infections (CDIs) and/or recurring CDIs (rCDIs).

24. The composition of claim 23, wherein the CDIs and/or rCDIs are caused by dysbiosis.

25. The composition of claim 19, wherein the bacterium is *E. coli* Nissle or *E. coli* T10.

* * * * *

SEQUENCE LISTING

<160> NUMBER OF SEQ ID NOS: 14

<210> SEQ ID NO 1
<211> LENGTH: 3641
<212> TYPE: DNA
<213> ORGANISM: Artificial Sequence
<220> FEATURE:
<223> OTHER INFORMATION: pEaat plasmid

<400> SEQUENCE: 1
aagcttaagt gatcattggc gcgccgtgta ggctggagct gcttcgaagt tcctatactt 60
tctagagaat aggaacttcg gaataggaac ttcaagatcc ccttattaga agaactcgtc 120
aagaaggcga tagaaggcga tgcgctgcga atcgggagcg gcgataccgt aaagcacgag 180
gaagcggtca gcccattcgc cgccaagctc ttcagcaata tcacgggtag ccaacgctat 240
gtcctgatag cggtccgcca cacccagccg gccacagtcg atgaatccag aaaagcggcc 300
attttccacc atgatattcg gcaagcaggc atcgccatgg gtcacgacga gatcctcgcc 360
gtcgggcatg cgcgccttga gcctggcgaa cagttcggct ggcgcgagcc cctgatgctc 420
ttcgtccaga tcatcctgat cgacaagacc ggcttccatc cgagtacgtg ctcgctcgat 480
gcgatgtttc gcttggtggt cgaatgggca ggtagccgga tcaagcgtat gcagccgccg 540
cattgcatca gccatgatgg atactttctc ggcaggagca aggtgagatg acaggagatc 600
ctgccccggc acttcgccca atagcagcca gtcccttccc gcttcagtga caacgtcgag 660
cacagctgcg caaggaacgc ccgtcgtggc cagccacgat agccgcgctg cctcgtcctg 720
cagttcattc agggcaccgg acaggtcggt cttgacaaaa agaaccgggc gcccctgcgc 780
tgacagccgg aacacggcgg catcagagca gccgattgtc tgttgtgccc agtcatagcc 840
gaatagcctc tccacccaag cggccggaga acctgcgtgc aatccatctt gttcaatcat 900
gcgaaacgat cctcatcctg tctcttgttc agatcatgat cccctgcgcc atcagatcct 960
tggcggcaag aaagccatcc agtttacttt gcagggcttc ccaaccttac cagagggcgc 1020
cccagctggc aattccggtt cgcttgctgt ccataaaacc gcccagtcta gctatcgcca 1080
tgtaagccca ctgcaagcta cctgctttct ctttgcgctt gcgttttccc ttgtccagat 1140
agcccagtag ctgacattca tccggggtca gcaccgtttc tgcggactgg ctttctacgt 1200
gttccgcttc ctttagcagc ccttgcgccc tgagtgcttg cggcagcgtg agcttcaaaa 1260
gcgctctgaa gttcctatac tttctagaga ataggaactt cgaactgcag gtcgacggat 1320
ctccggaata cgcgtttcga attcaagaga tctaaaggat cctaactcga gtaaggatct 1380
ccaggcatca aataaaacga aaggctcagt cgaaagactg ggcctttcgt tttatctgtt 1440
gtttgtcggt gaacgctctc tactagagtc acactggctc accttcgggt gggcctttct 1500
gcgtttatac ctagggcgtt cggctgcggc gagcggtatc agctcactca aaggcggtaa 1560

```
tacggttatc cacagaatca ggggataacg caggaaagaa catgtgagca aaaggccagc   1620
aaaaggccag gaaccgtaaa aaggccgcgt tgctggcgtt tttccatagg ctccgccccc   1680
ctgacgagca tcacaaaaat cgacgctcaa gtcagaggtg gcgaaacccg acaggactat   1740
aaagatacca ggcgtttccc cctggaagct ccctcgtgcg ctctcctgtt ccgaccctgc   1800
cgcttaccgg atacctgtcc gcctttctcc cttcgggaag cgtggcgctt tctcatagct   1860
cacgctgtag gtatctcagt tcggtgtagg tcgttcgctc caagctgggc tgtgtgcacg   1920
aaccccccgt tcagcccgac cgctgcgcct tatccggtaa ctatcgtctt gagtccaacc   1980
cggtaagaca cgacttatcg ccactggcag cagccactgg taacaggatt agcagagcga   2040
ggtatgtagg cggtgctaca gagttcttga agtggtggcc taactacggc tacactagaa   2100
ggacagtatt tggtatctgc gctctgctga agccagttac cttcggaaaa agagttggta   2160
gctcttgatc cggcaaacaa accaccgctg gtagcggtgg tttttttgtt tgcaagcagc   2220
agattacgcg cagaaaaaaa ggatctcaag aagatccttt gatcttttct acggggtctg   2280
acgctcagtg gaacgaaaac tcacgttaag ggattttggt catgactagt gcttggattc   2340
tcaccaataa aaaacgcccg gcggcaaccg agcgttctga acaaatccag atggagttct   2400
gaggtcatta ctggatctat caacaggagt ccaagcgagc tctcgaaccc cagagtgata   2460
tcttaatcca cgtatttcat cgcgactctt gaagtcaggc gcgtaataag ttcgtaagcg   2520
cttactttcg tcatttcagc gatacgttct acgggcaaac cttcgcccca taaaatgacc   2580
gggtccccgg ctttgtcctg cgcctgtgga cctaagtcta cgcagatcat atccatcgcg   2640
actcgcccga caatcggcac ttcgcgaccg ttcaccagca ctggcgtacc ggacggcgcg   2700
gcgcgcggat aaccatcgcc atagcccatc gcgactacgc caagacgagt atcacgttcg   2760
cttacccagg ttccaccata accgacaggc tctccggctt tatgctcacg cacggcaatc   2820
aggctggagg ttaaagacat gactggctga cagccaaaat cagcccctgt cgtgccatct   2880
tccagcggcg agacaccgta aagaatgatc cccggacgcg cccagtcaaa atgcgactgc   2940
ggccataaca aaatgccgcc tgatgccgca attgagcgtt gccccggttt accttcacaa   3000
aaggtgttga aaatatcgag ctgcttttca gtcgcgccgc tttgcggttc atcggcacgg   3060
gcgaagtgac taacaatgtt caccggctgg cggacatttt tacactggct cagacgctga   3120
taaaacgcct cggcctgttc cggcaatacg cccaaacggt gcattccggt atcgagcttc   3180
atccagacgg tgacaggctc tttaagttca gcgttttcga gggcgacaag ctgctcttca   3240
ttgtggactg cggtatgcag atgttcagcg gagatcgtcg gcaaatcgtc tgcttcaaaa   3300
aaaccttcca gtaacaaaat aggtcgcgtg ataccccccg cccgcagccg tagggcttct   3360
tcgagacggg caacgccaaa ggcgtcagca tcggggagcg ttcgcgcggt ctcaatcaga   3420
ccgtgaccgt aggcgttcgc tttcaccacc gcaaccagtt tactggcggg ggccagttca   3480
cgcagacgtt gcaggttgtg tcgcagagcg cggcggttaa tcaaaacagt tgccgcttgc   3540
atttgtattc cttttttca ggttctgccc accagtgcaa aacctcgcta aacagatatg   3600
accggagtat gctattccac atccagggat gggtttataa a                       3641
```

<210> SEQ ID NO 2
<211> LENGTH: 99
<212> TYPE: DNA
<213> ORGANISM: Artificial Sequence
<220> FEATURE:
<223> OTHER INFORMATION: alr promoter

<400> SEQUENCE: 2

```
tttataaacc catccctgga tgtggaatag catactccgg tcatatctgt ttagcgaggt     60

tttgcactgg tgggcagaac ctgaaaaaaa ggaatacaa                            99
```

<210> SEQ ID NO 3
<211> LENGTH: 1080
<212> TYPE: DNA
<213> ORGANISM: Artificial Sequence
<220> FEATURE:
<223> OTHER INFORMATION: alr ORF

<400> SEQUENCE: 3

```
atgcaagcgg caactgtttt gattaaccgc cgcgctctgc gacacaacct gcaacgtctg     60

cgtgaactgg cccccgccag taaactggtt gcggtggtga aagcgaacgc ctacggtcac    120

ggtctgattg agaccgcgcg aacgctcccc gatgctgacg cctttggcgt tgcccgtctc    180

gaagaagccc tacggctgcg ggcggggggt atcacgcgac ctattttgtt actggaaggt    240

ttttttgaag cagacgattt gccgacgatc tccgctgaac atctgcatac cgcagtccac    300

aatgaagagc agcttgtcgc cctcgaaaac gctgaactta aagagcctgt caccgtctgg    360

atgaagctcg ataccggaat gcaccgtttg ggcgtattgc cggaacaggc cgaggcgttt    420

tatcagcgtc tgagccagtg taaaaatgtc cgccagccgg tgaacattgt tagtcacttc    480

gcccgtgccg atgaaccgca aagcggcgcg actgaaaagc agctcgatat tttcaacacc    540

ttttgtgaag gtaaaccggg gcaacgctca attgcggcat caggcggcat tttgttatgg    600

ccgcagtcgc attttgactg ggcgcgtccg ggatcattc tttacggtgt ctcgccgctg    660

gaagatggca cgacaggggc tgattttggc tgtcagccag tcatgtcttt aacctccagc    720

ctgattgccg tgcgtgagca taaagccgga gagcctgtcg gttatggtgg aacctgggta    780

agcgaacgtg atactcgtct tggcgtagtc gcgatgggct atggcgatgg ttatccgcgc    840

gccgcgccgt ccggtacgcc agtgctggtg aacggtcgcg aagtgccgat tgtcgggcga    900

gtcgcgatgg atatgatctg cgtagactta ggtccacagg cgcaggacaa agccggggac    960

ccggtcattt tatggggcga aggtttgccc gtagaacgta tcgctgaaat gacgaaagta   1020

agcgcttacg aacttattac gcgcctgact tcaagagtcg cgatgaaata cgtggattaa   1080
```

<210> SEQ ID NO 4
<211> LENGTH: 85
<212> TYPE: DNA
<213> ORGANISM: Artificial Sequence
<220> FEATURE:
<223> OTHER INFORMATION: pNanA promoter

<400> SEQUENCE: 4

```
agatcgcatt ataagctttc tgtatggggt gttgcttaat tgatctggta taacaggtat     60

aaaggtatat cgtttatcag acaag                                           85
```

<210> SEQ ID NO 5
<211> LENGTH: 792
<212> TYPE: DNA
<213> ORGANISM: Artificial Sequence
<220> FEATURE:
<223> OTHER INFORMATION: NanR ORF

<400> SEQUENCE: 5

```
atgggcctta tgaacgcatt tgattcgcaa accgaagatt cttcacctgc aattggtcgc     60

aacttgcgta gccgcccgct ggcgcgtaaa aaactctccg aaatggtgga agaagagctg    120
```

```
gaacagatga tccgccgtcg tgaatttggc gaaggtgaac aattaccgtc tgaacgcgaa    180

ctgatggcgt tctttaacgt cgggcgtcct tcggtgcgtg aagcgctggc agcgttaaaa    240

cgcaaaggtc tggtgcaaat aaacaacggc gaacgcgctc gcgtctcgcg tccttctgcg    300

gacactatca tcggtgagct ttccggcatg gcgaaagatt tcctttctca tcccggtggg    360

attgcccatt tcgaacaatt acgtctgttc tttgaatcca gtctggtgcg ctatgcggct    420

gaacatgcca ccgatgagca aatcgatttg ctggcaaaag cactggaaat caacagtcag    480

tcgctggata acaacgcggc attcattcgt tcagacgttg atttccaccg cgtgctggcg    540

gagatccccg gtaacccaat cttcatggcg atccacgttg ccctgctcga ctggcttatt    600

gccgcacgcc caacggttac cgatcaggca ctgcacgaac ataacaacgt tagttatcaa    660

cagcatattg cgatcgttga tgcgatccgc cgtcatgatc ctgacgaagc cgatcgtgcg    720

ttgcaatcgc atctcaacag cgtctctgct acctggcacg ctttcggtca gaccaccaac    780

aaaaagaaat aa                                                        792
```

```
<210> SEQ ID NO 6
<211> LENGTH: 1094
<212> TYPE: DNA
<213> ORGANISM: Artificial Sequence
<220> FEATURE:
<223> OTHER INFORMATION: J23113-rbs4-NanR

<400> SEQUENCE: 6

tataaacgca gaaaggccca cccgaaggtg agccagtgtg actctagtag agagcgttca     60

ccgacaaaca acagataaaa cgaaaggccc agtctttcga ctgagccttt cgttttattt    120

gatgcctgga gatccttatt tctttttgtt ggtggtctga ccgaaagcgt gccaggtagc    180

agagacgctg ttgagatgcg attgcaacgc acgatcggct tcgtcaggat catgacggcg    240

gatcgcatca acgatcgcaa tatgctgttg ataactaacg ttgttatgtt cgtgcagtgc    300

ctgatcggta accgttgggc gtgcggcaat aagccagtcg agcagggcaa cgtggatcgc    360

catgaagatt gggttaccgg ggatctccgc cagcacgcgg tggaaatcaa cgtctgaacg    420

aatgaatgcc gcgttgttat ccagcgactg actgttgatt tccagtgctt ttgccagcaa    480

atcgatttgc tcatcggtgg catgttcagc cgcatagcgc accagactgg attcaaagaa    540

cagacgtaat tgttcgaaat gggcaatccc accgggatga gaaaggaaat ctttcgccat    600

gccggaaagc tcaccgatga tagtgtccgc agaaggacgc gagacgcgag cgcgttcgcc    660

gttgtttatt tgcaccagac ctttgcgttt taacgctgcc agcgcttcac gcaccgaagg    720

acgcccgacg ttaaagaacg ccatcagttc gcgttcagac ggtaattgtt caccttcgcc    780

aaattcacga cggcggatca tctgttccag ctcttcttcc accatttcgg agagtttttt    840

acgcgccagc gggcggctac gcaagttgcg accaattgca ggtgaagaat cttcggtttg    900

cgaatcaaat gcgttcataa ggcccataga tccgtcctgt gtgaagatcc gctagcataa    960

tccctaggac tgagctagcc atcagggatc tagatcgcat tataagcttt ctgtatgggg   1020

tgttgcttaa ttgatctggt ataacaggta taaaggtata tcgtttatca gacaagggat   1080

ctaaagagga gaaa                                                     1094
```

```
<210> SEQ ID NO 7
<211> LENGTH: 1923
<212> TYPE: DNA
<213> ORGANISM: Artificial Sequence
<220> FEATURE:
```

<223> OTHER INFORMATION: cadC-pCadBA amplifier

<400> SEQUENCE: 7

```
atgcaacaac ctgtagttcg cgttggcgaa tggcttgtta ctccgtccat aaaccaaatt     60
agccgcaatg ggcgtcaact taccccttgag ccgagattaa tcgatcttct ggttttcttt    120
gctcaacaca gtggcgaagt acttagcagg gatgaactta tcgataatgt ctggaagaga    180
agtattgtca ccaatcacgt tgtgacgcag agtatctcag aactacgtaa gtcattaaaa    240
gataatgatg aagatagtcc tgtctatatc gctactgtac caaagcgcgg ctataaatta    300
atggtgccgg ttatctggta cagcgaagaa gagggagagg aaataatgct atcttcgcct    360
cccccctatac cagaggcggt tcctgccaca gattctccct cccacagtct taacattcaa    420
aacaccgcaa cgccacctga acaatcccca gttaaaagca aacgattcac tacctttttgg    480
gtatggtttt ttttcctgtt gtcgttaggt atctgtgtag cactggtagc gttttcaagt    540
cttgatacac gtcttcctat gagcaaatcg cgtattttgc tcaatccacg cgatattgac    600
attaatatgg taaataaaag ttgtaacagc tggagttccc cgtatcagct ctcttacgcg    660
ataggcgtgg gtgatttggt ggcgacatca cttaacacct tctccacctt tatggtgcat    720
gacaaaatca actacaacat tgatgaaccg agcagttccg gtaaaacatt atctattgcg    780
tttgttaatc agtgccaata ccgtgctcaa caatgcttta tgtcgataaa attggtagac    840
aatgcagatg gttcaaccat gctggataaa cgttatgtca tcactaacgg taatcagctg    900
gcgattcaaa atgatttact ggagagttta tcaaaagcgt taaaccaacc gtggccacaa    960
cgaatgcagg agacgctcca gaaaattttg ccgcatcgtg gtgcgttatt aactaatttt   1020
tatcaggcac atgattattt actgcatggc gatgataaat cattgaaccg tgccagtgaa   1080
ttattaggtg agattgttca atcatcccca gaatttacct acgcgagagc agaaaaagca   1140
ttagttgata tcgtgcgcca ttctcaacat cctttagatg aaaaacaatt agcagcactg   1200
aacacagaaa tagataacat tgttacactg ccggaattga acaacctgtc cattatatat   1260
caaataaaag cggtcagtgc tctggtaaaa ggtaaaacag atgagtctta ccaggcgata   1320
aatactggca ttgatcttga aatgtcctgg ctaaattatg tgttgcttgg caaggtttat   1380
gaaatgaagg ggatgaaccg ggaagcagct gatgcatatc tcaccgcctt taatttacgc   1440
ccaggggcaa acaccctttta ctggattgaa aatggtatat tccagacttc tgttccttat   1500
gttgtacctt atctcgacaa atttcttgct tcagaataag gatctagact tctgttcctt   1560
atgttgtacc ttatctcgac aaatttcttg cttcagaata agtaactccg ggttgattta   1620
tgctcggaaa tatttgttgt tgagtttttg tatgttcctg ttggtataat atgttgcggc   1680
aatttatttg ccgcataatt tttattacat aaatttaacc agagaatgtc acgcaatcca   1740
ttgtaaacat taaatgttta tcttttcatg atatcaactt gcgatcctga tgtgttaata   1800
aaaaacctca agttctcact tacagaaact tttgtgttat ttcacctaat ctttaggatt   1860
aatccttttt tcgtgagtaa tcttatcgcc agtttggtct ggtcaggaaa taaagaggag   1920
aaa                                                                 1923
```

<210> SEQ ID NO 8
<211> LENGTH: 990
<212> TYPE: DNA
<213> ORGANISM: Artificial Sequence
<220> FEATURE:
<223> OTHER INFORMATION: cbh ORF native

<400> SEQUENCE: 8

```
atgtgtacag gattagcctt agaaacaaaa gatggattac atttgtttgg aagaaatatg     60
gatattgaat attcatttaa tcaatctatt atatttattc ctaggaattt taaatgtgta    120
aacaaatcaa acaaaaaaga attaacaaca aaatatgctg ttcttggaat gggaactatt    180
tttgatgatt atcctacctt tgcagatggt atgaatgaaa agggattagg gtgtgctggc    240
ttaaatttcc ctgtttatgt tagctattct aaagaagata tagaaggtaa aactaatatt    300
ccagtatata atttcttatt atgggtttta gctaatttta gctcagtaga agaggtaaag    360
gaagcattaa aaaatgctaa tatagtggat atacctatta gcgaaaatat tcctaataca    420
actcttcatt ggatgataag cgatataaca ggaaagtcta ttgtggttga acaaacaaag    480
gaaaaattaa atgtatttga taataatatt ggagtattaa ctaattcacc tacttttgat    540
tggcatgtag caaatttaaa tcaatatgta ggtttgagat ataatcaagt tccagaattt    600
aagttaggag atcaatcttt aactgcttta ggtcaaggaa ctggtttagt aggattacca    660
ggggacttta cacctgcatc tagatttata agagtagcat ttttaagaga tgcaatgata    720
aaaaatgata aagattcaat agacttaatt gaatttttcc atatattaaa taatgttgct    780
atggtaagag gatcaactag aactgtagaa gaaaaaagtg atcttactca atatacaagt    840
tgcatgtgtt tagaaaaagg aatttattat tataatacct atgaaaataa tcaaattaat    900
gcaatagaca tgaataaaga aaacttagat ggaaatgaaa ttaaaacata taaatacaac    960
aaaactttaa gtattaatca tgtaaattag                                     990
```

<210> SEQ ID NO 9
<211> LENGTH: 990
<212> TYPE: DNA
<213> ORGANISM: Artificial Sequence
<220> FEATURE:
<223> OTHER INFORMATION: cbh ORF codon optimised

<400> SEQUENCE: 9

```
atgtgtaccg gtttggcatt ggagaccaag gatggtctcc acttatttgg tcgcaatatg     60
gatattgagt atagctttaa ccaatcgatt atttttatcc cgcgcaactt taaatgcgta    120
aataaatcta ataagaaaga actgactacg aaatatgcgg tcctcggtat ggggacgatt    180
ttcgatgatt atcccacgtt tgcagacggc atgaacgaaa agggtctggg gtgtgcgggt    240
cttaattttc ctgtgtacgt cagttatagt aaggaagaca tcgagggaaa aaccaatatt    300
ccggtatata acttcttgct gtgggttctg gcaaatttta gctcagtcga agaagtgaag    360
gaagcgttaa aaaatgccaa tatcgtggat attccgatta gcgaaaacat tccgaatact    420
acgttgcact ggatgatctc ggacattact ggcaaaagca ttgtggtaga acagactaaa    480
gaaaaactga atgtcttcga caacaatatc ggggttttaa ccaattctcc gacttttgac    540
tggcatgtag ctaacttgaa tcagtatgtg ggactgcgtt ataaccaagt cccggagttc    600
aaactgggcg accagtcttt aaccgcgctg ggccagggca ccggcctggt ggggctgccg    660
ggcgacttca cccctgcgtc acgcttcatt cgcgtagcat tccttcgcga tgcgatgatt    720
aaaaatgaca aagacagcat tgacctgatc gagttctttc atattttaaa taatgtggct    780
atggtacggg gctctacgcg cactgtggaa gaaaagagcg acttgaccca gtatacctca    840
tgcatgtgcc tggaaaaagg catttactac tacaatactt atgaaaataa tcagatcaat    900
gccatcgata tgaacaaaga gaacctggac ggtaatgaaa ttaaaaccta taaatacaat    960
aaaacgctgt cgatcaatca tgtcaactaa                                     990
```

```
<210> SEQ ID NO 10
<211> LENGTH: 359
<212> TYPE: PRT
<213> ORGANISM: Artificial Sequence
<220> FEATURE:
<223> OTHER INFORMATION: Alr

<400> SEQUENCE: 10

Met Gln Ala Ala Thr Val Leu Ile Asn Arg Arg Ala Leu Arg His Asn
1               5                   10                  15

Leu Gln Arg Leu Arg Glu Leu Ala Pro Ala Ser Lys Leu Val Ala Val
            20                  25                  30

Val Lys Ala Asn Ala Tyr Gly His Gly Leu Ile Glu Thr Ala Arg Thr
        35                  40                  45

Leu Pro Asp Ala Asp Ala Phe Gly Val Ala Arg Leu Glu Glu Ala Leu
    50                  55                  60

Arg Leu Arg Ala Gly Gly Ile Thr Arg Pro Ile Leu Leu Leu Glu Gly
65                  70                  75                  80

Phe Phe Glu Ala Asp Asp Leu Pro Thr Ile Ser Ala Glu His Leu His
                85                  90                  95

Thr Ala Val His Asn Glu Glu Gln Leu Val Ala Leu Glu Asn Ala Glu
            100                 105                 110

Leu Lys Glu Pro Val Thr Val Trp Met Lys Leu Asp Thr Gly Met His
        115                 120                 125

Arg Leu Gly Val Leu Pro Glu Gln Ala Glu Ala Phe Tyr Gln Arg Leu
    130                 135                 140

Ser Gln Cys Lys Asn Val Arg Gln Pro Val Asn Ile Val Ser His Phe
145                 150                 155                 160

Ala Arg Ala Asp Glu Pro Gln Ser Gly Ala Thr Glu Lys Gln Leu Asp
                165                 170                 175

Ile Phe Asn Thr Phe Cys Glu Gly Lys Pro Gly Gln Arg Ser Ile Ala
            180                 185                 190

Ala Ser Gly Gly Ile Leu Leu Trp Pro Gln Ser His Phe Asp Trp Ala
        195                 200                 205

Arg Pro Gly Ile Ile Leu Tyr Gly Val Ser Pro Leu Glu Asp Gly Thr
    210                 215                 220

Thr Gly Ala Asp Phe Gly Cys Gln Pro Val Met Ser Leu Thr Ser Ser
225                 230                 235                 240

Leu Ile Ala Val Arg Glu His Lys Ala Gly Glu Pro Val Gly Tyr Gly
                245                 250                 255

Gly Thr Trp Val Ser Glu Arg Asp Thr Arg Leu Gly Val Val Ala Met
            260                 265                 270

Gly Tyr Gly Asp Gly Tyr Pro Arg Ala Ala Pro Ser Gly Thr Pro Val
        275                 280                 285

Leu Val Asn Gly Arg Glu Val Pro Ile Val Gly Arg Val Ala Met Asp
    290                 295                 300

Met Ile Cys Val Asp Leu Gly Pro Gln Ala Gln Asp Lys Ala Gly Asp
305                 310                 315                 320

Pro Val Ile Leu Trp Gly Glu Gly Leu Pro Val Glu Arg Ile Ala Glu
                325                 330                 335

Met Thr Lys Val Ser Ala Tyr Glu Leu Ile Thr Arg Leu Thr Ser Arg
            340                 345                 350

Val Ala Met Lys Tyr Val Asp
        355
```

<210> SEQ ID NO 11
<211> LENGTH: 263
<212> TYPE: PRT
<213> ORGANISM: Artificial Sequence
<220> FEATURE:
<223> OTHER INFORMATION: NanR

<400> SEQUENCE: 11

```
Met Gly Leu Met Asn Ala Phe Asp Ser Gln Thr Glu Asp Ser Ser Pro
1               5                   10                  15

Ala Ile Gly Arg Asn Leu Arg Ser Arg Pro Leu Ala Arg Lys Lys Leu
            20                  25                  30

Ser Glu Met Val Glu Glu Glu Leu Glu Gln Met Ile Arg Arg Arg Glu
        35                  40                  45

Phe Gly Glu Gly Glu Gln Leu Pro Ser Glu Arg Glu Leu Met Ala Phe
    50                  55                  60

Phe Asn Val Gly Arg Pro Ser Val Arg Glu Ala Leu Ala Ala Leu Lys
65                  70                  75                  80

Arg Lys Gly Leu Val Gln Ile Asn Asn Gly Glu Arg Ala Arg Val Ser
                85                  90                  95

Arg Pro Ser Ala Asp Thr Ile Ile Gly Glu Leu Ser Gly Met Ala Lys
            100                 105                 110

Asp Phe Leu Ser His Pro Gly Gly Ile Ala His Phe Glu Gln Leu Arg
        115                 120                 125

Leu Phe Phe Glu Ser Ser Leu Val Arg Tyr Ala Ala Glu His Ala Thr
    130                 135                 140

Asp Glu Gln Ile Asp Leu Leu Ala Lys Ala Leu Glu Ile Asn Ser Gln
145                 150                 155                 160

Ser Leu Asp Asn Asn Ala Ala Phe Ile Arg Ser Asp Val Asp Phe His
                165                 170                 175

Arg Val Leu Ala Glu Ile Pro Gly Asn Pro Ile Phe Met Ala Ile His
            180                 185                 190

Val Ala Leu Leu Asp Trp Leu Ile Ala Ala Arg Pro Thr Val Thr Asp
        195                 200                 205

Gln Ala Leu His Glu His Asn Asn Val Ser Tyr Gln Gln His Ile Ala
    210                 215                 220

Ile Val Asp Ala Ile Arg Arg His Asp Pro Asp Glu Ala Asp Arg Ala
225                 230                 235                 240

Leu Gln Ser His Leu Asn Ser Val Ser Ala Thr Trp His Ala Phe Gly
                245                 250                 255

Gln Thr Thr Asn Lys Lys Lys
            260
```

<210> SEQ ID NO 12
<211> LENGTH: 512
<212> TYPE: PRT
<213> ORGANISM: Artificial Sequence
<220> FEATURE:
<223> OTHER INFORMATION: CadC

<400> SEQUENCE: 12

```
Met Gln Gln Pro Val Val Arg Val Gly Glu Trp Leu Val Thr Pro Ser
1               5                   10                  15

Ile Asn Gln Ile Ser Arg Asn Gly Arg Gln Leu Thr Leu Glu Pro Arg
            20                  25                  30

Leu Ile Asp Leu Leu Val Phe Phe Ala Gln His Ser Gly Glu Val Leu
        35                  40                  45
```

-continued

```
Ser Arg Asp Glu Leu Ile Asp Asn Val Trp Lys Arg Ser Ile Val Thr
    50                  55                  60

Asn His Val Val Thr Gln Ser Ile Ser Glu Leu Arg Lys Ser Leu Lys
65                  70                  75                  80

Asp Asn Asp Glu Asp Ser Pro Val Tyr Ile Ala Thr Val Pro Lys Arg
                85                  90                  95

Gly Tyr Lys Leu Met Val Pro Val Ile Trp Tyr Ser Glu Glu Glu Gly
            100                 105                 110

Glu Glu Ile Met Leu Ser Ser Pro Pro Pro Ile Pro Glu Ala Val Pro
        115                 120                 125

Ala Thr Asp Ser Pro Ser His Ser Leu Asn Ile Gln Asn Thr Ala Thr
    130                 135                 140

Pro Pro Glu Gln Ser Pro Val Lys Ser Lys Arg Phe Thr Thr Phe Trp
145                 150                 155                 160

Val Trp Phe Phe Phe Leu Leu Ser Leu Gly Ile Cys Val Ala Leu Val
                165                 170                 175

Ala Phe Ser Ser Leu Asp Thr Arg Leu Pro Met Ser Lys Ser Arg Ile
            180                 185                 190

Leu Leu Asn Pro Arg Asp Ile Asp Ile Asn Met Val Asn Lys Ser Cys
        195                 200                 205

Asn Ser Trp Ser Ser Pro Tyr Gln Leu Ser Tyr Ala Ile Gly Val Gly
    210                 215                 220

Asp Leu Val Ala Thr Ser Leu Asn Thr Phe Ser Thr Phe Met Val His
225                 230                 235                 240

Asp Lys Ile Asn Tyr Asn Ile Asp Glu Pro Ser Ser Ser Gly Lys Thr
                245                 250                 255

Leu Ser Ile Ala Phe Val Asn Gln Cys Gln Tyr Arg Ala Gln Gln Cys
            260                 265                 270

Phe Met Ser Ile Lys Leu Val Asp Asn Ala Asp Gly Ser Thr Met Leu
        275                 280                 285

Asp Lys Arg Tyr Val Ile Thr Asn Gly Asn Gln Leu Ala Ile Gln Asn
    290                 295                 300

Asp Leu Leu Glu Ser Leu Ser Lys Ala Leu Asn Gln Pro Trp Pro Gln
305                 310                 315                 320

Arg Met Gln Glu Thr Leu Gln Lys Ile Leu Pro His Arg Gly Ala Leu
                325                 330                 335

Leu Thr Asn Phe Tyr Gln Ala His Asp Tyr Leu Leu His Gly Asp Asp
            340                 345                 350

Lys Ser Leu Asn Arg Ala Ser Glu Leu Leu Gly Glu Ile Val Gln Ser
        355                 360                 365

Ser Pro Glu Phe Thr Tyr Ala Arg Ala Glu Lys Ala Leu Val Asp Ile
    370                 375                 380

Val Arg His Ser Gln His Pro Leu Asp Glu Lys Gln Leu Ala Ala Leu
385                 390                 395                 400

Asn Thr Glu Ile Asp Asn Ile Val Thr Leu Pro Glu Leu Asn Asn Leu
                405                 410                 415

Ser Ile Ile Tyr Gln Ile Lys Ala Val Ser Ala Leu Val Lys Gly Lys
            420                 425                 430

Thr Asp Glu Ser Tyr Gln Ala Ile Asn Thr Gly Ile Asp Leu Glu Met
        435                 440                 445

Ser Trp Leu Asn Tyr Val Leu Leu Gly Lys Val Tyr Glu Met Lys Gly
    450                 455                 460
```

```
Met Asn Arg Glu Ala Ala Asp Ala Tyr Leu Thr Ala Phe Asn Leu Arg
465                 470                 475                 480

Pro Gly Ala Asn Thr Leu Tyr Trp Ile Glu Asn Gly Ile Phe Gln Thr
                485                 490                 495

Ser Val Pro Tyr Val Val Pro Tyr Leu Asp Lys Phe Leu Ala Ser Glu
            500                 505                 510


<210> SEQ ID NO 13
<211> LENGTH: 329
<212> TYPE: PRT
<213> ORGANISM: Artificial Sequence
<220> FEATURE:
<223> OTHER INFORMATION: Cbh

<400> SEQUENCE: 13

Met Cys Thr Gly Leu Ala Leu Glu Thr Lys Asp Gly Leu His Leu Phe
1               5                   10                  15

Gly Arg Asn Met Asp Ile Glu Tyr Ser Phe Asn Gln Ser Ile Ile Phe
            20                  25                  30

Ile Pro Arg Asn Phe Lys Cys Val Asn Lys Ser Asn Lys Lys Glu Leu
        35                  40                  45

Thr Thr Lys Tyr Ala Val Leu Gly Met Gly Thr Ile Phe Asp Asp Tyr
    50                  55                  60

Pro Thr Phe Ala Asp Gly Met Asn Glu Lys Gly Leu Gly Cys Ala Gly
65                  70                  75                  80

Leu Asn Phe Pro Val Tyr Val Ser Tyr Ser Lys Glu Asp Ile Glu Gly
                85                  90                  95

Lys Thr Asn Ile Pro Val Tyr Asn Phe Leu Leu Trp Val Leu Ala Asn
            100                 105                 110

Phe Ser Ser Val Glu Glu Val Lys Glu Ala Leu Lys Asn Ala Asn Ile
        115                 120                 125

Val Asp Ile Pro Ile Ser Glu Asn Ile Pro Asn Thr Thr Leu His Trp
    130                 135                 140

Met Ile Ser Asp Ile Thr Gly Lys Ser Ile Val Val Glu Gln Thr Lys
145                 150                 155                 160

Glu Lys Leu Asn Val Phe Asp Asn Asn Ile Gly Val Leu Thr Asn Ser
                165                 170                 175

Pro Thr Phe Asp Trp His Val Ala Asn Leu Asn Gln Tyr Val Gly Leu
            180                 185                 190

Arg Tyr Asn Gln Val Pro Glu Phe Lys Leu Gly Asp Gln Ser Leu Thr
        195                 200                 205

Ala Leu Gly Gln Gly Thr Gly Leu Val Gly Leu Pro Gly Asp Phe Thr
    210                 215                 220

Pro Ala Ser Arg Phe Ile Arg Val Ala Phe Leu Arg Asp Ala Met Ile
225                 230                 235                 240

Lys Asn Asp Lys Asp Ser Ile Asp Leu Ile Glu Phe Phe His Ile Leu
                245                 250                 255

Asn Asn Val Ala Met Val Arg Gly Ser Thr Arg Thr Val Glu Glu Lys
            260                 265                 270

Ser Asp Leu Thr Gln Tyr Thr Ser Cys Met Cys Leu Glu Lys Gly Ile
        275                 280                 285

Tyr Tyr Tyr Asn Thr Tyr Glu Asn Asn Gln Ile Asn Ala Ile Asp Met
    290                 295                 300

Asn Lys Glu Asn Leu Asp Gly Asn Glu Ile Lys Thr Tyr Lys Tyr Asn
305                 310                 315                 320
```

```
Lys Thr Leu Ser Ile Asn His Val Asn
                325


<210> SEQ ID NO 14
<211> LENGTH: 1539
<212> TYPE: DNA
<213> ORGANISM: Artificial Sequence
<220> FEATURE:
<223> OTHER INFORMATION: CadC ORF

<400> SEQUENCE: 14

atgcaacaac ctgtagttcg cgttggcgaa tggcttgtta ctccgtccat aaaccaaatt     60

agccgcaatg ggcgtcaact tacccttgag ccgagattaa tcgatcttct ggttttcttt    120

gctcaacaca gtggcgaagt acttagcagg gatgaactta tcgataatgt ctggaagaga    180

agtattgtca ccaatcacgt tgtgacgcag agtatctcag aactacgtaa gtcattaaaa    240

gataatgatg aagatagtcc tgtctatatc gctactgtac caaagcgcgg ctataaatta    300

atggtgccgg ttatctggta cagcgaagaa gagggagagg aaataatgct atcttcgcct    360

ccccctatac cagaggcggt tcctgccaca gattctccct cccacagtct taacattcaa    420

aacaccgcaa cgccacctga acaatcccca gttaaaagca aacgattcac taccttttgg    480

gtatggtttt ttttcctgtt gtcgttaggt atctgtgtag cactggtagc gttttcaagt    540

cttgatacac gtcttcctat gagcaaatcg cgtattttgc tcaatccacg cgatattgac    600

attaatatgg taaataaaag ttgtaacagc tggagttccc cgtatcagct ctcttacgcg    660

ataggcgtgg gtgatttggt ggcgacatca cttaacacct tctccacctt tatggtgcat    720

gacaaaatca actacaacat tgatgaaccg agcagttccg gtaaaacatt atctattgcg    780

tttgttaatc agtgccaata ccgtgctcaa caatgcttta tgtcgataaa attggtagac    840

aatgcagatg gttcaaccat gctggataaa cgttatgtca tcactaacgg taatcagctg    900

gcgattcaaa atgatttact ggagagttta tcaaaagcgt taaaccaacc gtggccacaa    960

cgaatgcagg agacgctcca gaaaattttg ccgcatcgtg gtgcgttatt aactaatttt   1020

tatcaggcac atgattattt actgcatggc gatgataaat cattgaaccg tgccagtgaa   1080

ttattaggtg agattgttca atcatcccca gaatttacct acgcgagagc agaaaaagca   1140

ttagttgata tcgtgcgcca ttctcaacat cctttagatg aaaaacaatt agcagcactg   1200

aacacagaaa tagataacat tgttacactg ccggaattga acaacctgtc cattatatat   1260

caaataaaag cggtcagtgc tctggtaaaa ggtaaaacag atgagtctta ccaggcgata   1320

aatactggca ttgatcttga aatgtcctgg ctaaattatg tgttgcttgg caaggtttat   1380

gaaatgaagg ggatgaaccg ggaagcagct gatgcatatc tcaccgcctt taatttacgc   1440

ccaggggcaa acacccttta ctggattgaa aatggtatat tccagacttc tgttccttat   1500

gttgtacctt atctcgacaa atttcttgct tcagaataa                          1539
```